US012584162B2

(12) United States Patent
Ku et al.

(10) Patent No.: US 12,584,162 B2
(45) Date of Patent: Mar. 24, 2026

(54) HYDROXYMETHYLATION ANALYSIS OF CELL-FREE NUCLEIC ACID SAMPLES FOR ASSIGNING TISSUE OF ORIGIN, AND RELATED METHODS OF USE

(71) Applicant: CLEARNOTE HEALTH, INC., San Diego, CA (US)

(72) Inventors: Chin-Jen Ku, San Francisco, CA (US); Francois Collin, San Francisco, CA (US); Patrick Arensdorf, Palo Alto, CA (US); Samuel Levy, San Diego, CA (US)

(73) Assignee: ClearNote Health, Inc., San Diego, CA (US)

( * ) Notice: Subject to any disclaimer, the term of this patent is extended or adjusted under 35 U.S.C. 154(b) by 0 days.

(21) Appl. No.: 17/740,212

(22) Filed: May 9, 2022

(65) Prior Publication Data

US 2023/0095582 A1 Mar. 30, 2023

Related U.S. Application Data

(63) Continuation of application No. 16/450,744, filed on Jun. 24, 2019, now abandoned.

(60) Provisional application No. 62/688,975, filed on Jun. 22, 2018, provisional application No. 62/746,237, filed on Oct. 16, 2018.

(51) Int. Cl.

| | |
|---|---|
| ***C12Q 1/6827*** | (2018.01) |
| ***C12Q 1/6809*** | (2018.01) |
| ***G16B 20/20*** | (2019.01) |
| ***G16B 40/10*** | (2019.01) |
| ***G16H 50/30*** | (2018.01) |

(52) U.S. Cl.

CPC ......... *C12Q 1/6827* (2013.01); *C12Q 1/6809* (2013.01); *G16B 20/20* (2019.02); *G16B 40/10* (2019.02); *G16H 50/30* (2018.01); *C12Q 2537/164* (2013.01); *C12Q 2600/154* (2013.01); *C12Q 2600/166* (2013.01); *C12Q 2600/172* (2013.01)

(58) Field of Classification Search

CPC ............ C12Q 2600/154; C12Q 1/6809; C12Q 2537/164

See application file for complete search history.

(56) References Cited

U.S. PATENT DOCUMENTS

| | | | |
|---|---|---|---|
| 2014/0322707 A1 | 10/2014 | He et al. | |
| 2016/0017419 A1 | 1/2016 | Chiu et al. | |
| 2017/0298427 A1 | 10/2017 | Buis et al. | |

FOREIGN PATENT DOCUMENTS

| | | | |
|---|---|---|---|
| WO | 2016008451 A1 | 1/2016 | |
| WO | 2017176630 A1 | 10/2017 | |
| WO | 2017201606 A1 | 11/2017 | |
| WO | WO2018099418 A1 | 6/2018 | |
| WO | WO-2019246625 A1 * | 12/2019 | ........... C12Q 1/6809 |

OTHER PUBLICATIONS

"Epigenetic Cell Counting", Epiontis, downloaded www.empiontis.com, Dec. 24, 2016, 1-2.

"PCT Search Report and Written Opinion, PCT/US2019/038765", Oct. 28, 2019.

Chakravarthy, Ankur, et al., "Pan-cancer deconvolution of tumour composition using DNA methylation", Nature Communications | DOI: 10.1038/s41467-018-05570-1, 2018, 1-13.

Chen, Yuting, et al., "Tissue-independent and tissue-specific patterns of DNA methylation alteration in Cancer", Epigenetics & Chromatin 9:10, 2016, 1-11.

Cobos, Francisco Avila, et al., "Computational deconvolution of transcriptomics data from mixed cell populations", Bioinformatics, 34(11), Jan. 16, 2018, 1969-1979.

Ecsedi, Szilvia, et al., "5-Hydroxymethylcytosine (5hmC), or How to Identify your Favorite Cell", Epigenomes, 2,3; doi:10.3390/epigenomes2010003;, Jan. 2018, 1-20.

Globish, Daniel, et al., "Tissue Distribution of 5-Hydroxymethylcytosine and Search for Active Demethylation Intermediates", PloS One 5(12): e15367, doi:10.1371/journal.pone.0015367, Dec. 2010, 1-9.

Houseman, Eugene Andres, "Reference-free cell mixture adjustments in analysis of DNA methylation data", Bioinformatics, vol. 30, No. 10, 2014, 1431-1439.

Iouseman, E. Andres, et al., "Reference-free deconvolution of DNA methylation data and mediation by cell composition effects", BMC Bioinformatics 17:259, 2016, 1-15.

(Continued)

*Primary Examiner* — Joseph G. Dauner

(74) *Attorney, Agent, or Firm* — Doreen Yatko Trujillo; VLP Law Group LLP

(57) ABSTRACT

A method is provided for probabilistically assigning a tissue of origin to a nucleic acid in a sample, e.g., DNA in a cell-free fluid sample obtained from a human subject. A hydroxymethylation profile is generated for the sample DNA and then compared across a reference data set of hydroxymethylation profile vectors, where each hydroxymethylation profile vector identifies the hydroxymethylation profile at a specific reference locus, the tissue-specific gene associated with the reference locus, and the tissue with which the gene and reference locus are associated. A tissue of origin can be probabilistically assigned to the sample nucleic acid using the results of the comparison. Other methods of use are also provided.

16 Claims, No Drawings

(56) References Cited

OTHER PUBLICATIONS

Juan, David, et al., "Epigenomic Co-localization and Co-evolution Reveal a Key Role for 5hmC as a Communication Hub in the Chromatin Network of ESCs", Cell Reports 14,, Feb. 9, 2016, 1246-1257.

Koestler, Devin C., et al., "Blood-based profiles of DNA methylation predict the underlying distribution of cell types", Epigenetics vol. 8, Issue 8, Aug. 2013, 816-826.

Koestler, Devin C., et al., "Improving cell mixture deconvolution by identifying optimal DNA methylation libraries (IDOL)", BMC Bioinformatics 17:120, 2016, 1-21.

Lehmann-Werman, Roni , et al., "Identification of Tissue-Specific Cell Death Using Methylation Patterns of Circulating DNA", PNAS Early Edition, 1-9, doi:10/173/pnas.1519286113;, Feb. 9, 2016, 1-9.

Li, Wenshuai, et al., "5-Hydroxymethylcytosine signatures in circulating cell-free DNA as diagnostic biomarkers for human cancers", Cell Research—Xibao Yanjiu, vol. 27, No. 10, Sep. 19, 2017, pp. 1243-125.

Li, Weiwei, et al., "Distribution of 5-Hydroxymethylcytosine in Different Human Tissues", Nucl. Acids 2011, Article ID 870726, doi: 10.4061/2011/870726, Apr. 15, 2011, 1-6.

Lin, I-Hsuan, et al., "Correlated 5-Hydroxymethylcytosine (5hmC) and Gene Expression Profiles Underpin Gene and Organ-Specific Epigenetic Regulation in Adult Mouse Brain and Liver", PloS One 12(1): e0170779. doi: 10.1371/journal.pone.0170779, Jan. 26, 2017, 1-25.

Nestor, Colm E., et al., "Tissue Type is a Major Modifier of the 5-Hydroxymethylcytosine Content of Human Genes", Genome Research 22; Cold Spring Harbor Laboratory Press, 2012, 467-477.

Ponnaluri, V.K. Chaithanya, et al., "Association of 5-Hydroxymethylation and 5-Methylation of DNA Cytosine with Tissue-Specific Gene Expression", Epigenetics 12(2): doi:10.1080/15592294.2016.1265713;, Dec. 2, 2017, 123-138.

Salas, Lucas A., et al., "Tracing human stem cell lineage during development using DNA methylation", Genome Research, 28, 2018, 1285-1295.

Snyder, Matthew W., et al., "Cell-free DNA Comprises an In Vivo Nucleosome Footprint that Informs its Tissues-Of-Origin", Cell 164, Jan. 14, 2016, 57-68.

Song, Chun-Xiao, et al., "5-Hydroxymethylcytosine signatures in cell-free DNA provide information about tumor types and stages", Cell Research—Xibao Yanjiu, vol. 27, No. 10, Aug. 18, 2017, pp. 1231-1242.

Sproul, Duncan, et al., "Tissue of Origin Determines Cancer-Associated CpG Island Promoter Hypermethylation Patterns", Genome Biology 13:R84, 2012, 1-16.

Teschendorff, Andrew E., "Cell-type deconvolution in epigenomewide association studies: a review and recommendations", Epigenomics 9(5), 2017, 757-768.

Song, Chun-Xiao, et al., "5-Hydroxymethylcytosine signatures in cellfree DNA provide information about tumor types and stages", Cell Research—Xibao Yanjiu, vol. 27, No. 10, XP055540434, GB, CN ISSN: 1001-0602, DOI: 10.1038/cr.2017.106 ; & Chun-Xiao Song:, Aug. 18, 2017, pp. 1231-1242.

Chim S S C et al: "Detection of the placental epigenetic signature of the maspin gene in maternal plasma", Proceedings of the National Academy of Sciences (PNAS), National Academy of Sciences, vol. 102, No. 41, Oct. 11, 2005 (Oct. 11, 2005), pp. 14753-14758, XP002355638, ISSN: 0027-8424, DOI: 10.1073/PNAS.0503335102.

European partial search report, EP25191950.2, dated Jan. 22, 2026, 17 pages.

* cited by examiner

HYDROXYMETHYLATION ANALYSIS OF CELL-FREE NUCLEIC ACID SAMPLES FOR ASSIGNING TISSUE OF ORIGIN, AND RELATED METHODS OF USE

CROSS-REFERENCE TO RELATED APPLICATIONS

This application is a continuation of U.S. patent application Ser. No. 16/450,744, filed Jun. 24, 2019, which claims priority under 35 U.S.C. § 119(e)(1) to provisional U.S. application Ser. No. 62/688,975, filed Jun. 22, 2018, and Ser. No. 62/746,237, filed Oct. 16, 2018. The disclosures of the foregoing applications are incorporated by reference in their entireties.

TECHNICAL FIELD

The present invention relates generally to biotechnology, and more particularly relates to applications of the epigenetic analysis of cell-free DNA. The invention finds utility in the fields of genomics, medicine, diagnostics, and epigenetic research.

BACKGROUND

In many fields related to medicine, such as diagnostics, theranostics, and patient monitoring, there is an ongoing need for more precise methods of analyzing biological samples and extracting useful information from those analyses, with the often competing goals of accuracy and efficiency. Analytical methods should lend themselves to high speed processing and automation, yield the necessary results quickly and cost effectively, and provide high sensitivity and specificity. Furthermore, the information provided by an analytical method should be maximally useful. In a method for analyzing a patient's DNA, for example, it would be ideal if that method were capable of rapidly providing information sufficient to diagnose the existence of a pathological state.

Recently, researchers in the field of epigenetics have suggested a test in which the methylation state of a patient's DNA is used to ascertain the likelihood that the DNA derives from a particular tissue or organ. See, e.g., Sun et al. (2015) *Proc. Natl. Acad. Sci.* 112(40): E5503-E5512, which describes the use of genome-wide bisulfite sequencing to generate methylation profiles for various tissues, and Kang et al. (2017) *Genome Biology* 18:53, describing the use of DNA methylation patterns to identify the tissue of origin of tumor-derived DNA.

Cell-free DNA analysis is a relatively recent phenomenon that has the advantage of being noninvasive, enabling the evaluation of patient samples without need for surgery. However, analysis of cell-free DNA also presents unique challenges, particularly since cell-free DNA samples are very small and typically contain only a few nanograms of DNA per mL of plasma. The problem is compounded when cell-free DNA is used in conjunction with epigenetic analyses, in which relatively rare DNA modifications, such as 5-methylcytosine and the even rarer 5-hydroxymethylcytosine, require detection.

There is, accordingly, an ongoing need in the art for methods of epigenetic analysis applicable to cell-free DNA, where the information provided includes the tissue or organ of origin for a particular gene body or fragment thereof.

SUMMARY OF THE INVENTION

As the field of epigenetics has evolved, the detection of a rare DNA modification, 5-hydroxymethylcytosine (5hmC), has proved to be potentially as important as the detection of the methylated analog, i.e., 5-methylcytosine:

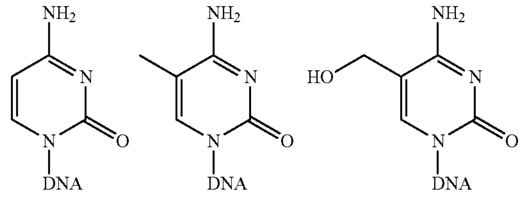

Cytosine 5mC 5hmC

The occurrence of 5hmC is much less frequent than that of 5 mC, at a ratio typically approximating 10:1, depending on tissue type (see Nestor et al. (2012) *Genome Biology* 13: R84), with 5mC representing about 1% of all DNA bases. Bisulfite sequencing does not distinguish between 5mC and 5hmC, and, therefore, other methods for individually detecting 5mC and 5hmC residues are necessary. As 5hmC appears far less often than 5mC, any method for detecting 5hmC needs to exhibit high efficiency, with respect to the fraction of all 5hmC residues that are identified, as well as high selectivity, meaning that substantially all residues identified as 5hmC should, in fact, be 5hmC residues. The molecular function of 5hmC is just beginning to be understood, although it has been established that 5hmC is involved in a variety of processes, including transcription, DNA demethylation, and, in the case of aberrant 5hmC patterns, in tumorigenesis. See Tahiliani et al. (2009) *Science* 324(5929):930-035 (2009); Guo et al. (2011) *Cell* 145:423-434; Wu et al. (2011) *Genes & Development* 25:679-684; Ko et al. (2010) *Nature* 468:839-843; and Robertson et al. (2011) *Biochem. Biophys. Res. Comm.* 411(1):40-3. It is also known that 5hmC is a stable DNA modification, formed from the catalytic oxidation of 5mC by a Ten-Eleven Translocation (TET) enzyme such as TET1.

The invention is predicated on the use of 5-hydroxymethylation ("hydroxymethylation") profiles to probabilistically assign a tissue of origin to a nucleic acid in a sample, generally DNA in a sample fluid obtained from a human subject. The method involves comparison of a hydroxymethylation profile generated for the sample nucleic acid with a reference data set that comprises reference hydroxymethylation profiles at each of a plurality of reference loci, with each reference locus contained within a genomic region associated with a tissue-specific gene. The aforementioned loci are sometimes referred to herein as "biomarker loci," "hydroxymethylation biomarker loci," or "hydroxymethylation biomarkers."

The loci at which hydroxymethylation states are determined, as just noted, are hydroxymethylation biomarker loci each contained within a genomic region associated with a particular tissue, with varying degrees of correlation (or specificity). That is, while certain genes have similar hydroxymethylation patterns in all cells (i.e., house-keeping genes), other genes have differentially represented hydroxymethylation patterns in various tissues throughout the body, and reference loci associated with these "differentially represented" (DR) genes are of primary interest herein. The reason for this is that hydroxymethylation patterns associated with genes that are highly represented in a particular tissue are most useful in a tissue determination.

In some embodiments, the reference loci are associated with DR genes in which gene expression levels also have specificity to a particular tissue, i.e., genes that are differentially represented that are also "differentially expressed" (DE).

The information in the reference data set is in the form of a plurality of hydroxymethylation vectors, with each hydroxymethylation vector identifying at least the following: the hydroxymethylation state at a specific reference locus; the tissue-specific gene associated with the reference locus; and the tissue with which the gene and reference locus are associated. The invention thus involves analyzing a nucleic acid in a sample by first generating its hydroxymethylation profile and then assessing similarity across the large hydroxymethylome data set that makes up the reference data set. A detailed comparison of the sample's hydroxymethylation profile across the hydroxymethylation vectors in the reference data set yields information pertaining to tissue type. That information may be a probability that the nucleic acid derives from a particular tissue type, or it may be in the form of two or more probabilities indicating that the nucleic acid analyzed originates from two or more corresponding different tissue types. With multiple nucleic acids undergoing analysis, as is the case with DNA fragments in a cell-free fluid sample obtained from a subject, the information may include a projection of overall proportion of tissue types corresponding to the DNA fragments analyzed.

In one embodiment, then, a method is provided for probabilistically assigning a tissue of origin to a nucleic acid in a cell-free fluid sample obtained from a human subject, the method comprising:

(a) generating a hydroxymethylation profile of the nucleic acid;

(b) comparing the hydroxymethylation profile of the nucleic acid with each of a plurality of reference hydroxymethylation profiles in a reference data set, each reference hydroxymethylation profile corresponding to a reference locus contained within a genomic region associated with a tissue-specific gene;

(c) identifying at least one reference locus having a reference hydroxymethylation profile that is substantially similar to the detected hydroxymethylation profile in (a); and (d) probabilistically assigning at least one tissue of origin to the nucleic acid based on the at least one reference locus identified in (c) and the corresponding tissue-specific gene.

In one aspect of the embodiment, the method comprises probabilistically assigning at least one tissue of origin to each of a plurality of DNA fragments in the cell-free fluid sample.

In another aspect of this embodiment, the reference data set contains hydroxymethylation profiles of reference loci associated with a plurality of tissue-specific genes.

In another aspect of the embodiment, each reference locus is contained within a differentially hydroxymethylated genomic region associated with a tissue-specific gene. Differentially hydroxymethylated regions can differ with respect to hydroxymethylation profile in one or more respects, e.g., with respect to density, pattern, or the like, and, in general, are functionally associated with a corresponding tissue-specific gene.

In an additional aspect of the embodiment, at least one reference locus is contained within a gene body or a component thereof.

In an additional aspect of the embodiment, at least one reference locus is contained within a genomic annotation feature outside of the gene, e.g., a promoter, an enhancer, a transcription initiation site, a transcription stop site, or a DNA binding site such as a silenced region (e.g., an STR or ERV region) or a transcription factor binding site, e.g., a transcriptional repressor binding site or a transcription enhancer binding site.

In a further aspect of the embodiment, at least one of the reference loci in the reference set are contained within a CTCF binding site.

In a further aspect of the embodiment, the reference hydroxymethylation profiles comprise a hydroxymethylation profile of at least one reference locus associated with a tissue-specific gene, wherein the tissue-specific gene is associated with a human tissue type (or functional, organ, anatomical and related cell-lineage groupings of types, e.g. digestive, brain and myeloid- or lymphoid-derived) including: adipose; adrenal gland; bladder; bone marrow; brain; breast; colon; cerebral cortex; cervical; uterine; digestive; endometrial; epididymal; esophageal; Fallopian tube; gall bladder; gastrointestinal; heart muscle; hypothalamus; kidney; liver; lung; lymph nodes; ovary; pancreas; parathyroid gland; placenta; prostate; salivary; seminal vesicle; skeletal muscle; smooth muscle; skin; spleen; stomach; testis; thyroid gland; and tonsil.

In another aspect of the embodiment, each reference locus is contained within a differentially represented gene comprising AARD, ADARB1, AKR1B10, ANAPC7, APCDD1L-AS1, APOA1BP, CALHM2, CASC3, CLEC2L, COL4A5, CRYM-AS1, EPHA3, FAHD2B, FKBP9L, FOPNL, GNG11, GSN, GSTTP2, GTSF1, IAH1, KCNMB1, KIAA1644, LAMC1, LINC00310, LOC100506394, LOC100507066, LOC493754, MAP1B, MGC27382, MIR5695, NENF, NT5DC3, P2RX1, PCP4, PGM5, PLCD4, PTGFR, RBFOX3, RPL30, SCARA3, SLIT3, SNX29P1, SPATA4, ST8SIA1, TBX4, TXNRD1, VCL, VPS72, WFDC3, ZNF791, ADAMTS20, AFF2, ANKRD18B, ANKRD18DP, ANKRD20A5P, ANKRD20A8P, ANKRD26P1, ANKRD30BP2, ANKRD34B, ANKRD34C, ATP6V0B, AVPR1A, BLOC1S3, BOLL, BRIP1, C5orf63, CA1, CALB1, CALCR, CCDC39, CCDC96, CDCA5, CDH12, CDH9, CEACAM8, CENPE, CENPK, CFL1, CHAT, COMMD5, COMMD8, CRISP1, CRISP2, CSN1S1, CSN1S2AP, CT64, CXCR2, CXorf30, DAZL, DCDC1, DRGX, DSG1, DUT, DUX2, DUX4L2, DUX4L3, DYTN, EDA2R, EFCAB3, EPOR, EVX2, F13A1, FCAR, FCER1A, FKBP1B, FOXA2, GABPB1-AS1, GABRA1, GABRA4, GABRG1, GALNTL6, GFER, GFI1, GPR152, GPR158-AS1, GPRC6A, GRM1, GRP, GRXCR1, GYPA, HAGHL, HCRTR2, HEPHL1, HJURP, HK3, HMBS, HORMAD2, ID4, IL17RA, IL18RAP, KCNC2, KCNK18, KIF18A, KIF20B, KLHL1, LEF1-AS1, LHX1, LHX3, LHX8, LINC00273, LINC00558, LINC00645, LINC00648, LLPH, LOC100129620, LOC100270679, LOC100505776, LOC100506422, LOC284801, LOC392232, LOC399815, LOC401074, LOC401134, LOC440040, LOC440970, LOC642236, LOC727924, LOC728012, LPO, LRRIQ1, MAGEA11, MAGOHB, MEFV, MIF4GD, MIR548A3, MIR5692A1, MMP8, MMP9, MMRN1, MRGPRE, MS4A3, MSRB1, MYO3A, NCOR1P1, NDST3, NDST4, NHLRC4, NOXRED1, NPAP1, NUF2, OR8G1, OR8U8, ORC6, OSM, OTX2, PAX3, PBK, PCDH8, PDCL2, POTEA, PROK2, PRR7, RAB24, RAX, RBM46, RGS18, RGS19, RIMS2, RNF175, RRM2, SATB2-AS1, SCN11A, SCRT2, SERPINB10, SGOL2, SIX1, SKA3, SKOR1, SLC22A16, SLC4A10, SLC5A7, SLC5A8, SLCO6A1, SNAP91, SPAG16, SPATA16, SPDL1, SPINK13, STPG2, STXBP5L, TARM1, TDRD5, TEX15, THSD7B, TMPRSS11A, TMPRSS11B, TMPRSS11D, TRIM58, TUBB4B, UNC13C, USP6, VRK1, VSTM1, VWDE, WDR49, WFDC8, WFDC9, ZIC5, ZNF230, ZNF300P1, ZNF470, ZNF502, ZNF599, ZPBP, Clorf159, CCDC42B, CCDC8, CD248, CERCAM, CNTN2, CRB2, EVI5L, FZD9, HAPLN2, HPDL, LINC00575, LOC284950, LOC339666, LRIT1, PLEKHH1, SHISA2, SLC46A2, TFAP2E, TMEM235, TNFRSF18, ZFP36, Colon UR, Clorf109, CACNA1F, COX7B, EFNB1, FGL2, F1134208, GNRH1, GSTT1, IL12A, KCND1, KDELR1, LAT, LOC100130992, LOC100287042, LOC401242, MRPL10, NT5C3B, PDZD4, PPYR1, RAD51D, RBMXL3, RENBP, SCNN1B, SERPINB5, SLC9A6, XBP1, ZNF189, ABR, ADPRHL1, ASB18, ATP1A3, CCDC74A, CDH13, CHRNA10, CORO6, FSD2, GALNT16, GDAP1L1, GJA3, GLUD1P3, GPRC5B, LOC100506343, LRRC37A6P, LRRC4, MUL1, MYOM2, NDUFB8, NT5DC2, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PXDNL, RHPN1-AS1, RPL3L, SGCG, TIMM21, TNNT1, TOR4A, UBAC1, WDR37, ZNF12, ZNF213, ZNF550, ZNF843, ZNF844, AGAP6, ASTN1, BBS2, C18orf56, C19orf45, CINP, DGKI, DPY30, DROSHA, FAM169A, FAM66D, FONG, GALNT15, GDAP1, GHRH, GUSBP4, HIF1AN, IFIT1B, INTS2, JAKMIP2-AS1, KGFLP2, LINC00297, LINC00707, LOC100288069, LOC100507140, LPHN3, LYPD1, LZIC, MIR548T, MRAP, NTRK3, PDE6D, PPP1R17, PRSS54, PRSS55, PTPRA, RGS7, SNRNP35, SUGT1P1, UBE2Z, WDR47, WDYHV1, ZNF114, ZNF556, ZNF610, ABP1, AGPAT9, APH1B, ASAP2, ATP4B, ATP6V1A, BBOX1, BCRP3, C11orf63, C13orf35, C16orf96, C19orf21, CA12, CCDC64, COL4A3, CXCL14, CYS1, EIF4E2, EPB41L1, EVC, FIGNL2, FUT3, GALNT14, GLIS2, GUSBP11, HAVCR1, HOXC5, INADL, KATNA1, L2HGDH, LOC100130238, LOC100506305, LOC284100, LOC654433, LYG1, MORN4, MTNR1A, PAQR5, PARG, PAX2, PAX8, PLA2G15, POU5F1, PRKAB1, RNF113B, SENP8, SETD3, SLC22A2, SLC25A30, SLC9A3, SULT1C2, TBC1D7, TSPAN33, ABCB4, ABCC11, ABCC2, ABCG5, ABCG8, ACADSB, ACSM5, AGMO, AGXT2L1, AKR1C2, AKR1C4, AKR1D1, AMDHD1, APOB, APOH, APOM, AQP9, ARHGEF40, ASGR2, ASPG, ATP2B2, BCO2, BDH1, C3, C3P1, C5, C8A, C8B, C8orf74, CASA, CABP2, CALR3, CD7, CDK10, CEACAM16, CES1, CFH, CFHR4, CHP1, CIDEB, CLPTM1L, CLRN3, CPN2, CREB3L3, CROCCP2, CYP2B6, CYP2C18, CYP2C19, CYP2C9, CYP2E1, CYP3A5, CYP7A1, DGAT2, DHODH, DPYS, DRG2, ECHS1, EDC4, EI24, ENO1, F13B, F2, F7, F9, FASN, FETUB, GCH1, GCKR, GDPD4, GFRA1, GHR, GLT1D1, GPAM, GSDMB, HAL, HAO1, HAPLN4, HPD, HPX, HYLS1, IGF2, IGF2-AS, IGFBP1, ISY1-RAB43, ITIH1, ITIH2, ITIH4, IVD, KLC4, LBP, LEFTY1, LIPG, LOC100288122, LOC284865, LPAL2, LRRC16B, MASP1, MGMT, MST1, MTTP, NAT9, NBR2, NELFE, NR1I2, NUP88, OSGIN1, PAH, PARD6A, PCSK9, PEX19, PGLYRP2, PHGDH, PHYH, PKLR, PLA2G12B, PLG, PNPLA3, POFUT1, POLR1E, PON1, PPL, PRAP1, PRKAG3, PROC, PUSS, RANBP10, RCE1, RND1, RNF123, RORC, RPUSD4, SAA2-SAA4, SCP2, SEC16B, SERPINA6, SERPINC1, SKIV2L, SLC13A5, SLC22A25, SLC25A20, SLC27A5, SLC30A10, SLCO1B3, SMLR1, SNAPC5, SPP2, SRD5A1, STAT2, STEAP3, SULT2A1, TFR2, THNSL2, TIAF1, TM6SF2, TMEM45A, TMPRSS6, TTC31, TTC38, UROC1, XYLB, ZCCHC9, ZSCAN22, ADAMS, ANKRD50, ARGLU1, ARL6, ARSJ, BMP5, BMPR2, BTG3, Clorf140, CALM2, CCDC102B, CCNL1, CCR5, CD36, CHN1, CLIC2, CPEB2, CRBN, CYP4Z2P, CYYR1, DACH1, DGKE, DGKH, DISP1, DOCK4, ETV1, EXOC1, FAM204A, FAT4, FGD5-AS1, FLJ34503, FRYL, GBP1P1, GNB4, GPR110, GPR116, HMCN1, HMGN1, IFI44, IL15, ITGA2, KAL1, KDR, KITLG, KLHL41, LDB2, LINC00032, LINC00240, LINC00551, LINC00657, LOC100131234, LOC100505495, LOC100507217, LOC643733, LPAR6, MGP, ODF2L, PEAK1, PKIA, PLEKHA1, PLEKHG7, PTPRB, QKI, RAD21, RALA, RAP2A, RCC1, SAMD12, SESTD1, SH3GLB1, SKAP2, SLC35A5, SMURF2, SPRED1, SRSF1, TCF4, TIGD4, TMEM207, TMOD3, UHMK1, VEGFC, XIST, YIPF5, ZC2HC1A, ZEB1, AKNA, ANKRD34A, C14orf183, CCDC107, CD180, CD3G, CD74, CDC42SE2, CHMP7, COTL1, CYTH1, FAIM3, FAM65B, GPX4, GSTP1, HLA-DMA, HLA-DOA, HLA-DPB1, HVCN1, ICAM2, ICOS, IL6, ITGB7, LOC100130557, MDM4, METTL21D, MGC16275, MIR548AN, NAPSB, RPL39L, RPS11, SEPT6, SH2D3C, TAP1, TEAD2, TMEM60, TNFRSF9, TRAF1, UBAC2, UCP2, WDR87, ACTA2, ADAMTS5, AQP11, ATP1B2, BICD1, C7, CDH3, CDON, COL14A1, HS3ST1, KLF4, LEMD1-AS1, LINC00672, LOC100129617, LOC339298, LRRC17, NDP, NTF3, OMD, PDGFRA, PGR, ROBO4, RWDD4, SCD5, SERPINE2, SLC25A17, SNCAIP, SYTL4, TENM4, TSPAN5, UBXN8, ZNF93, ALDH1L2, ANKEF1, ASUN, B3GALNT2, BBIP1, C6orf201, CASP9, CCDC110, CCDC65, CDK14, CELA2B, CELA3B, CFTR, CHMP4C, CHRNA7, CLCN3, CLDN1, CPA3, CUZD1, DNAJC10, DNAJC3, EIF2S1, EIF4EBP1, ERO1LB, FAIM, FAM160A1, FAM162A, FAM221A, FAM24B-CUZD1, GARS, GUCA1C, HSPA13, IFRD1, INTS6, KCTD16, LINC00339, LMAN1, LOC154092, LOC201651, LOC644838, LYPD6B, MAN1A2, MGC72080, MKNK1, MPP6, MSRB2, NAA16, NOMO2, OSTC, PEX7, PGRMC2, PIK3CB, PLA2G12A, PM20D1, PPP1R9A, PRRC1, PRSS3, RNPC3, SCFD1, SCRN3, SERPINI2, SH3YL1, SLC16A7, SLC33A1, SLC4A4, SORBS2, SRBD1, SSR1, TDH, TDP2, TMEM51-AS1, TMEM65, TRHDE, TRIM44, UGT2A3, UMOD, WDFY2, WHAMM, XPOT, ACER2, ADAM12, ADCY10, ADCY7, ADORA2B, AIM1L, AKNAD1, ALDH3B2, AMOT, ANGPT2, APOLD1, ATF3, ATG9B, ATP6V1C2, ATRIP, BCAR3, BCAR4, BEAN1, BPGM, BTBD19, C11orf70, C16orf46, C16orf74, C17orf98, C1QTNF6, C2orf62, C2orf83, C3orf52, C4orf26, C4orf51, C6orf99, C7orf71, C9orf129, CACNA2D3-AS1, CAPN6, CCDC125, CEP41, CLEC7A, CPA4, CSF3R, CTSL3P, CXorf56, CYP19A1, DACT2, DDX59, DLX3, DLX5, DLX6-AS1, DNMT1, DUSP4, EBI3, EDARADD, EPAS1, EPS8L1, ERVFRD-1, ERVMER34-1, ETV3, ETV4, EXTL1, EZR, FAM184A, FAM89A, FANCE, FBLN1, FBN2, FHDC1, FOLR1, GATA2, GATA3, GBA, GCM1, GDPD3, GLDN, GM2A, GPR156, GSG1, GSTA3, GSTA4, HELLS, HOPX, HSD11B2, HSPBAP1, IGF2BP3, IGSF5, ISM2, KATNBL1, KIAA1467, KIAA1609, KISS1, KLRG2, L1TD1, LCMT1, LCTL, LIN28B, LINC00439, LOC100131564, LOC100506746, LOC100527964, LOC151475, LOC152578, LOC284551, LOC643441, MB21D2, MED12, METTL21C, MFSD2B, MGC16121, MINA, MORC4, MSANTD3, MUTYH, NOS3, NVL, NXF1, OLR1, OSCP1, OSTCP1, P2RY6, PCBP1-AS1, PDE6A, PGC, PGF, PLA1A, PLAC4, PPP1R14D, PSG11, PSG2, PSG6, PSG7, PSG8, PTGES, PVRL3-AS1, PVRL4, PWWP2B, RAB36, RHO, RNF222, RPSAP58, RS1, SBF2-AS1, SCIN, SDC1, SEMA3F, SEMA6D, SEPT12, SH2D7, SH3GLB2, SLC13A4, SLC26A2, SLC2A1-AS1, SMAGP, SMARCB1, SMIM13, SNX12, SP6, SPESP1, SPIRE2, ST3GAL6-AS1, SVEP1, SYT8, TENM3, TLR3, TMEM216, TMEM218, TMEM52B, TMPRSS7, TP63, TPRXL, TRIM29, TRPV5, TUFT1, USHBP1, VAMPS, VGLL1, WBP2NL, XRCC2, ZDHHC1, ZNF320, ZNF331, ZNF354B, ZNF468, ZNF525, ZNF702P, ZNF90, ZP3, ZSWIM2, ZSWIM7, ABCC4, ACPP, ALDH1A2, ANKRD66, AP1B1P1, ARG2, BEND4, C1orf85, C6orf132, C6orf52, CHRNA2, COQ7, EVX1, EYA2, F1139080, GDEP, HMGN2P46, ISX, KLKP1, MCCC2, MEAF6, MFSD4, MRPS23, NCAPD3, OACYLP, OAZ3, OR51E2, PAK1IP1, PCAT1, PI15, PPP1R7, PSMA4, SCNN1G, SLC14A1, SLC26A3, SLC2A12, SLC30A4, SLC35F2, TMEM79, TPM3P9, TTC12, USP50, ZNF350, ZNF532, ZNF589, AKIP1, ARHGEF26-AS1, ATG4A, BOLAS, CHMP4A, DHH, EPPK1, FCHSD1, GADL1, GCC1, GIPC3, HIGD2B, HTR3C, LINC00654, LOC91948, OLFML3, PTGES3L, WSCD2, ZNF202, ZNF205-AS1, ZNF426, ACOT1, C12orf54, CREB3, DDN, FAM50A, FNDC4, GORASP1, GUCA1B, IMPDH2, LINC00284, LOC100128076, LOC100128682, LOC100131434, LRP10, LRRC55, LRRC73, NOTO, RNF112, RTBDN, SIGLEC8, TNN, TRIM50, UBE2T, ZNF391, ZNF792, ALX4, AQP2, ATAD3B, C11orf85, CABLES2, CCDC114, CCDC27, CCNF, CD300C, CILP, DES, DMRT1, DNAJB8-A51, DRD4, EFCAB6-AS1, FAM153B, FAM163B, FGD2, HSD17B3, IFI27L1, IGFN1, ITPR3, KCNK15, KIFC2, KRT78, KRT82, LOC100506385, LOC283914, LOC284661, LOC399829, LOC653712, LOC728716, MAGED2, MYH16, MYLK2, NPTX2, PLK5, PMS2CL, PNPLA1, PODNL1, POLD1, PRMT8, PTPRVP, RD3, RIMS4, RNU6-81, RPL26L1, SALL4, SERPINA10, SPATA31E1, STAB1, SULT4A1, TCERG1L, TEKT4P2, THEG, TMEM130, TPO, UPK3B, WASH3P, WRAP53, ZNF280B, or ZNF793.

In a related aspect, each reference locus is contained within a differentially represented, differentially expressed gene comprising AARD, ADARB1, AKR1B10, CRYM-AS1, EPHA3, GTSF1, KCNMB1, MAP1B, NT5DC3, P2RX1, PCP4, PGM5, PLCD4, PTGFR, RBFOX3, SCARA3, SLIT3, SNX29P1, ST8SIA1, TBX4, TXNRD1, VCL, WFDC3, ABCA13, AZU1, CA1, CEACAM8, CLEC6A, DAZL, DRGX, DYTN, ELANE, FCAR, GFI1, GYPA, HK3, IL18RAP, LINC00333, LINC00550, LINC00558, LIPN, LOC100129620, LOC442028, LPO, MEFV, MMP8, MMP9, MPO, MS4A3, MYB, MYO1F, NCOR1P1, NME8, OR8U8, OSCAR, PARPBP, PAX3, PDCL2, PRDM13, PROK2, RGS18, RGS21, RRM2, RXFP2, SERPINB10, SLC22A16, SPATA16, SPI1, SPTA1, TARM1, TMPRSS15, TRIM58, VSTM1, XKR3, ASPHD1, BRSK1, CCDC177, CNTN2, HAPLN2, KCNJ10, KIF1A, LGI3, NCAN, NR2E1, RHBDL3, TMEM151A, TMEM235, TMEM59L, ZNF488, FGL2, SCNN1B, ADPRHL1, ASB18, ATP1A3, CDH13, CORO6, FSD2, GALNT16, GJA3, MYOM2, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB5, PCDHGB6, PCDHGB7, PXDNL, RPL3L, SGCG, TNNT1, ASTN1, DGK1, BBOX1, BCRP3, CA12, COL4A3, CXCL14, CYS1, EVC, FIGNL2, GALNT14, GLIS2, HAVCR1, LOC100130238, PAQR5, PAX2, PAX8, PLA2G15, SLC22A2, SLC9A3, SULT1C2, TSPAN33, ABCC2, ABCG5, ABCG8, AHSG, AKR1C4, AMDHD1, APOH, ASGR1, ASGR2, C3P1, C8A, C8B, C9, CASA, CFHR4, CPN2, CREB3L3, CYP2B6, CYP2C9, CYP2E1, CYP3A4, DHODH, F12, F2, F7, GC, HAL, HPD, HPX, INHBC, ITIH1, ITIH2, ITIH3, KNG1, LBP, PGLYRP2, PLG, PROC, PRODH2, SERPINA6, SERPINC1, SLC13A5, SLC22A1, SLC25A47, SLC27A5, SULT2A1, TFR2, TMPRSS6, UROC1, ANXA3, BMP5, CYP4Z2P, DRAM1, FMO2, GNA15, IDOL KCNS3, LIMCH1, MBIP, PAPSS2, PCDH17, RSPH4A, RTKN2, TRPC6, ACAP1, AKNA, ARHGAP9, BCL11B, BIRC3, CARD11, CD180, CD37, CD3E, CD3G, CD40, CETP, CIITA, CLEC2D, CNR2, CXCR5, DOCK10, ETS1, GPR132, GPR18, ICAM2, ICOS, ITGB7, ITK, KIAA1551, KLHL6, LCK, LINC00426, LY86, MDS2, MEOX2, MX2, NAPSB, PATL2, PCED1B-AS1, PIK3CD, PLVAP, POU2F2, SCIMP, SCML4, SLFN12L, SMAP2, SP110, SPIB, TLR10, TMC8, TMEM156, TNFAIP8, TNFRSF9, TNFSF11, TRAF1, TRIM22, UCP2, ZC3H12D, ABCA10, ACSS3, ADAMTS5, AQP11, C7, CDH3, CDON, CLDN11, COL14A1, COLEC11, ESR2, FAM198B, FZD3, GALNT10, GLI2, GSTM5, HS3ST1, LEMD1-AS1, LHX9, LRRC17, MCHR1, MRC2, NTF3, OMD, PDGFRA, PGR, PKNOX2, PTCH2, RWDD4, SCD5, SERPINE2, SIMC1, SLC25A17, SNCAIP, SULF2, TENM4, TSPAN5, TTC8, UBXN8, ALDH1L2, ANKEF1, ASNS, B3GALNT2, BCAT1, CASP9, CCDC110, CELA2B, CELA3B, CFTR, CHMP4C, CLDN1, CNIH3, COCH, CUZD1, DEFB1, EGF, EIF4EBP1, ERP27, FAM24B-CUZD1, FBXW12, GUCA1C, KCTD16, KIAA1324, LINC00339, LNX2, MKNK1, NAA16, NPHS1, PAIP2B, PM20D1, PRSS3, SCGN, SEL1L, SERPINI2, SH3YL1, SLC33A1, SLC4A4, TC2N, TDH, TMEM51-AS1, TRHDE, UMOD, ADAM12, ATG9B, ATP6V1C2, BCAR4, BMP1, BPGM, CSF3R, CYP11A1, CYP19A1, DACT2, DEPDC1B, DLX5, EBI3, GCM1, GPR78, GSTA3, IGF2BP3, IGSF5, ISM2, KISS1, KRT23, LIN28B, MMP11, PGF, PSG11, PSG2, PSG3, PSG6, PSG7, PSG8, SPTLC3, TPRXL, ZFAT, ZNF554, ABCC4, ACPP, ALOX15B, ANO7, AP1B1P1, ARG2, BEND4, C6orf132, C6orf52, CANT1, CASZ1, CBFA2T2, CHRM1, CHRNA2, COL26A1, EVX1, EYA2, FAM135A, HMGN2P46, KLK2, KLKP1, MME, MPPED2, MUC12, NANS, NCAPD3, NEFH, NIPAL3, OACYLP, OR51E2, PAK1IP1, PDE9A, PI15, PMEPA1, POTEF, RDH11, SCNN1G, SIM2, SLC14A1, SLC22A3, SLC2A12, SLC30A4, SLC35F2, SLC37A1, SLC39A6, SPDEF, STEAP2, THSD4, TMEM79, TPM3P9, TXNDC16, URB1, VIPR1, ZNF350, ZNF532, ZNF613, ZNF649, ZNF761, ZNF827, GADL1, GIPC3, PTGES3L, WSCD2, CCDC27, DMRT1, DNAJC5G, FBXO24, IGLL1, MOV10L1, SEPT14, THEG, or TTC16.

In a related aspect of the embodiment, the plurality of reference hydroxymethylation profiles in the reference set comprises, for each of a plurality of human tissue types, at least one reference locus in each of a plurality of tissue-specific genes associated with the human tissue type.

The generated hydroxymethylation profile for the nucleic acid sample and the reference hydroxymethylation profiles, as indicated above, generally include hydroxymethylation density, where the hydroxymethylation density may be calculated as the ratio of 5hmC residues to total cytosines, including both modified and unmodified cytosines. The comparison that is carried out can focus on the extent of similarity between the detected 5hmC density versus the reference 5hmC densities. When the detected 5hmC density is sufficiently similar to a reference 5hmC density at one or more of the tissue-specific loci, as determined using established criteria known or available to those in the art, a tissue of origin is probabilistically assigned to the nucleic acid. Additional sample-versus-reference comparisons can be carried out with respect to other hydroxymethylation features to refine the analysis and narrow the uncertainty inherent in the calculated tissue assignment. For example, the detected hydroxymethylation profile and the reference hydroxymethylation profiles may also be compared with respect to the pattern of 5hmC occurrence, where the pattern may be the relative location of two or more 5hmC residues within the locus and/or the specific location of the 5hmC residues within the locus. The profiles may additionally be compared with respect to the total number of 5mC residues, the relative locations of two or more 5hmC residues, and/or to the identification of a 5hmC site as hemi-hydroxymethylated or fully hydroxymethylated.

In another embodiment of the invention, a method is provided for detecting a condition of a tissue or organ in a human subject, where the condition of the tissue or organ is associated with or can be derived from the hydroxymethylation profile of DNA in a cell-free fluid sample taken from the subject. The method comprises:

(a) generating a hydroxymethylation profile for DNA in a cell-free fluid sample obtained from the subject;
(b) comparing the hydroxymethylation profile generated in (a) with each of a plurality of reference hydroxymethylation profiles in a reference set, each reference hydroxymethylation profile corresponding to (i) a reference locus associated with a tissue-specific gene and (ii) a condition of a specific tissue or organ; and
(c) based on the comparison of the hydroxymethylation profile generated for the sample with the reference hydroxymethylation profiles, identifying the condition of the specific tissue or organ in the subject.

In a further embodiment, a method is provided for monitoring changes in the condition of a tissue or organ in a human subject. The method comprises:

(a) generating an initial hydroxymethylation profile at one or more loci of DNA fragments in a cell-free fluid sample obtained from the subject, where the hydroxymethylation profile is associated with an initial condition of a tissue or organ;
(b) at a later time, generating a subsequent hydroxymethylation profile at the same one or more loci in a cell-free fluid sample obtained from the subject; and
(c) comparing the subsequent hydroxymethylation profile with the initial hydroxymethylation profile to detect a change in the condition of a tissue or organ.

In one aspect of this embodiment, the change in the condition of a tissue or organ may be an improvement or a decline.

In another aspect of this embodiment, the change in the condition of a tissue or organ may be evaluated in the context of assessing the efficacy of a therapeutic intervention.

In a further aspect of this embodiment, the change in the condition of a tissue or organ may be associated with changes in gene expression over time.

In a related aspect of the embodiment, the method further comprises repeating the evaluation at discrete time points within an extended evaluation period. That is, step (b) is repeated one or more additional times to monitor the progression of a condition, disease, or disorder associated with the tissue or organ.

In another related aspect of the embodiment, the method further comprises making a diagnosis, a treatment decision, or a prognosis based on a detected change in condition.

In another related aspect of the embodiment, the method further includes comparing the initial hydroxymethylation profile, the subsequent hydroxymethylation profile, or both the initial and subsequent hydroxymethylation profiles, to a plurality of reference hydroxymethylation profiles in a reference data set, each reference hydroxymethylation profile corresponding to a reference locus contained within a differentially hydroxymethylated genomic region associated with a tissue-specific gene.

In another embodiment of the invention, an improved method is provided for analyzing a cell-free DNA sample obtained from human plasma in which cell-free DNA fragments in the sample are isolated, amplified, and sequenced, wherein the improvement comprises identifying contamination of the sample with genomic material originating from peripheral blood mononuclear cells (PBMCs) by:

(a) generating a hydroxymethylation profile of DNA fragments in the cell-free sample; and
(b) comparing the hydroxymethylation profile generated in (a) with each of a plurality of reference hydroxymethylation profiles in a reference set, each reference hydroxymethylation profile associated with a reference locus corresponding to a tissue-specific gene, wherein the reference hydroxymethylation profiles include at least one PBMC hydroxymethylation profile; and
(c) identifying, from the comparison, the presence of genomic material originating from PBMCs.

In one aspect of the embodiment, the method further includes estimating the level of PBMC genomic contamination from the comparison in step (b). It will be appreciated that PBMC genomic contamination may be seen in cell-free samples as a result of post-collection PBMC lysis ex vivo, i.e., after sample collection. The method is thus useful as a measure of sample quality and an assessment as to whether a particular sample is suitable for use in cell-free DNA analyses.

In another aspect of the embodiment, the method further includes providing a correction vector for a cell-free DNA analysis based on a known hydroxymethylation vector for PBMC DNA, where the hydroxymethylation vector comprises a plurality of reference hydroxymethylation profiles corresponding to PBMC DNA. The correction vector can be used to offset, lower, or subtract the effects of poor sample quality due to PBMC DNA contamination, e.g., from post-collection PBMC lysis. The correction vector, providing that PBMC sub-type hydroxymethylation data is included in the vector, can also be used to specifically identify the proportions of PBMC sub-types in cell-free DNA contamination, including their activation or state.

In an additional aspect of the embodiment, the aforementioned correction vector is used to calibrate and normalize absolute counting measures, such as mutation load or fragment count.

In a further aspect of the embodiment, the correction vector is used to calibrate and normalize relative proportions of specific species of molecules, e.g., to adjust the variant allele frequency (VAF) and minor allele frequency (MAF) values determined for circulating tumor DNA (ctDNA), fetal DNA, or pathogen DNA.

In another embodiment, the invention provides a method for probabilistically assigning a tissue of origin to cell-free DNA in a sample obtained from a human subject, where the method comprises:

(a) generating a hydroxymethylation profile of DNA in the sample by:
(i) adding an affinity tag to only 5-hydroxymethylcytosine residues in the cell-free DNA;

(ii) enriching for DNA molecules that are tagged with the affinity tag by binding to a support; and (iii) sequencing the enriched DNA molecules to provide a map with each 5-hydroxymethylcytosine site identified;

(b) comparing the hydroxymethylation profile generated in (a) with each of a plurality of reference hydroxymethylation profiles in a reference data set, each reference hydroxymethylation profile associated with a reference locus in a differentially hydroxymethylated genomic region associated with a tissue-specific gene, (c) identifying at least one reference locus in the reference data set having a reference hydroxymethylation profile that is substantially similar to the generated hydroxymethylation profile; and (d) assigning at least one tissue of origin to each sequenced DNA molecule based on the at least one reference locus identified in (c) and the corresponding tissue-specific gene.

In another embodiment of the invention, a method is provided for determining whether a human subject is predisposed to develop an abnormal condition of a tissue or organ, where the condition of the tissue or organ is associated with the hydroxymethylation profile of a nucleic acid. The method comprises:

(a) generating a hydroxymethylation profile at one or more loci of DNA fragments in a cell-free fluid sample obtained from the subject;

(b) comparing the detected hydroxymethylation profile with a plurality of reference hydroxymethylation profiles in a reference set each associated with (i) a reference locus on a tissue-specific gene and (ii) a condition of the tissue indicating a predisposition to develop an abnormal condition of the specific tissue or organ; and (c) identifying a predisposition to develop the abnormal condition of the tissue from the comparison in (b).

In a further embodiment of the invention, a method is provided for differentiating DNA fragments associated with different tissues of origin in a sample of cell-free DNA obtained from a human subject, the method comprising:

(a) generating hydroxymethylation profiles of each of a plurality of nucleic acids in the cell-free DNA sample;

(b) comparing each hydroxymethylation profile with a plurality of reference hydroxymethylation profiles in a reference set each associated with a specific reference locus on a tissue-specific gene; and (c) differentiating nucleic acids originating from different tissues based on the comparison in (b).

In an exemplary aspect of the foregoing embodiment, the reference set comprises two or more reference sets selected from Set 3A, Set 3B, Set 3C, Set 3D, Set 3E, Set 3F, Set 3G, Set 3H, Set 3I, Set 3J, Set 3K, Set 3L, Set 3M, Set 3N, Set 3O, Set 3P, Set 3Q, Set 3R, and Set 3S, as set forth in Tables 1 through 19, infra.

In a further embodiment, any of the foregoing methods additionally comprise determining at least one of: nucleic acid length; nucleic acid fragment distribution; methylation pattern; and nucleosome positioning.

DETAILED DESCRIPTION OF THE INVENTION

The invention provides a method for probabilistically assigning a tissue of origin to a nucleic acid in a cell-free fluid sample, e.g., a cell-free DNA sample obtained from a human patient. Related methods and systems are also provided, involving diagnosis, prognosis, patient monitoring, and other methods. The invention assesses the similarity of a detected hydroxymethylation profile of a nucleic acid across a large reference set of hydroxymethylation profiles, i.e., a hydroxymethylome data set containing hydroxymethylation data for a plurality of loci on each of a plurality of tissue-specific genes, for a plurality of tissue types.

1. Terminology

Unless defined otherwise, all technical and scientific terms used herein have the meaning commonly understood by one of ordinary skill in the art to which the invention pertains. Specific terminology of particular importance to the description of the present invention is defined below. Other relevant terminology is defined in International Patent Publication No. WO 2017/176630 to Quake et al. for "Non-invasive Diagnostics by Sequencing 5-Hydroxymethylated Cell-Free DNA." The aforementioned patent publication as well as all other patent documents and publications referred to herein are expressly incorporated by reference.

In this specification and the appended claims, the singular forms "a," "an" and "the" include plural referents unless the context clearly dictates otherwise. Thus, for example, "a locus" refers not only to a single locus but also to two or more different loci, "a component" refers to a single component as well as a combination of two or more components, and the like.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

The term "hydroxymethylated" refers to the presence of at least one 5-hydroxymethylcytosine (5hmC) residue in a nucleic acid, i.e., a cytosine residue to which a hydroxymethyl group has been added at the 5' carbon.

The term "sample" as used herein relates to a sample derived from a biological fluid, cell, tissue, or organ of a human subject, comprising a nucleic acid or a mixture of nucleic acids. Generally, although not necessarily, the sample is a blood sample such as a whole blood sample, a serum sample, or a plasma sample. Nucleic acid samples herein may be complex in that they may contain multiple different molecules that contain nucleic acid sequences.

The term "biological sample" as used herein relates to a sample derived from a biological fluid, cell, tissue, or organ of a human subject, comprising a mixture of biomolecules including proteins, peptides, lipids, nucleic acids, and the like. Generally, although not necessarily, the sample is a blood sample such as a whole blood sample, a serum sample, or a plasma sample.

A "nucleic acid sample" as that term is used herein refers to a biological sample comprising nucleic acids. The nucleic acid sample may be a cell-free nucleic acid sample that comprises nucleosomes, in which case the nucleic acid sample is sometimes referred to herein as a "nucleosome sample." The nucleic acid sample may also be comprised of cell-free DNA wherein the sample is substantially free of histones and other proteins, such as will be the case following cell-free DNA purification. The nucleic acid samples herein may also contain cell-free RNA.

A "sample fraction" refers to a subset of an original biological sample, and may be a compositionally identical portion of the biological sample, as when a blood sample is divided into identical fractions. Alternatively, the sample fraction may be compositionally different, as will be the case when, for example, certain components of the biological sample are removed, with extraction of cell-free nucleic acids being one such example.

As used herein, the term "cell-free nucleic acid" encompasses both cell-free DNA and cell-free RNA, where the cell-free DNA and cell-free RNA may be in a cell-free fraction of a biological sample comprising a body fluid. The body fluid may be blood, including whole blood, serum, or plasma, or it may be urine, cyst fluid, or another body fluid. In many instances, the biological sample is a blood sample, and a cell-free nucleic acid sample is extracted therefrom using now-conventional means known to those of ordinary skill in the art and/or described in the pertinent texts and literature; kits for carrying out cell-free nucleic acid extraction are commercially available (e.g., the AllPrep® DNA/RNA Mini Kit and QIAamp® DNA Blood Mini Kit, both available from Qiagen®, or the MagMAX® Cell-Free Total Nucleic Acid Kit and the MagMAX® DNA Isolation Kit, available from ThermoFisher Scientific). Also see, e.g., Hui et al. Fong et al. (2009) *Clin. Chem.* 55(3):587-598.

As used herein, the term "cell-free DNA" (cfDNA) refers to DNA in a cell-free fraction or extract of a biological sample comprising a body fluid. Cell-free DNA may be highly fragmented and generally has a median size that is below 1 kb (e.g., in the range of 50 bp to 500 bp, 80 bp to 400 bp, or 100 bp to 1,000 bp), although fragments having a median size outside of this range may be present (in Newman et al. (2014) *Nat. Med.* 20: 548-54), a fragment size of 165 bp to 250 bp is reported). Cell-free DNA may contain circulating tumor DNA (ctDNA), i.e., tumor DNA circulating freely in the blood of a cancer patient, or circulating fetal DNA (if the subject is a pregnant female). cfDNA can be obtained by centrifuging whole blood to remove all cells, and then isolating the DNA from the remaining plasma or serum. Such methods are well known (see, e.g., Lo et al. (1998) *Am. J. Hum. Genet.* 162:768-75). Cell-free DNA is predominantly double-stranded, but can be made single-stranded by denaturation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Of particular interest herein are modified cytosine residues, including 5-methylcytosine and oxidized forms thereof, such as 5-hydroxymethylcytosine, 5-formylcytosine, and 5-carboxymethylcytosine.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, and up to about 10,000 or more bases composed of nucleotides, e.g., deoxyribonucleotides or ribonucleotide. Nucleic acids may be produced enzymatically, chemically synthesized, or naturally obtained.

The term "oligonucleotide" as used herein denotes a single-stranded multimer of nucleotide of from about 2 to 200 nucleotides, up to 500 nucleotides in length.

Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.).

The terms "duplex" and "duplexed" are used interchangeably herein to describe two complementary polynucleotides that are base-paired, i.e., hybridized together. A DNA duplex is referred to herein as "double-stranded DNA" or "dsDNA" and may be an intact molecule or a molecular segment. For example, the dsDNA herein referred to as barcoded and adapter-ligated is an intact molecule, while the dsDNA formed between the nucleic acid tails of proximity probes in a proximity extension assay is a dsDNA segment.

The term "strand" as used herein refers to a single strand of a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, "positive" and "negative" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "primer" refers to a synthetic oligonucleotide, which, upon forming a duplex with a polynucleotide template, is capable of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Like "primers," used to prime DNA replication reactions, "adapters" are also short synthetic oligonucleotides that serve a specific purpose in a biological analysis. Adapters can be single-stranded or double-stranded, although the preferred adapters herein are double-stranded. In one embodiment, an adapter may be a hairpin adapter (i.e., one molecule that base pairs with itself to form a structure that has a double-stranded stem and a loop, where the 3' and 5' ends of the molecule ligate to the 5' and 3' ends of a double-stranded DNA molecule, respectively). In another embodiment, an adapter may be a Y-adapter. In another embodiment, an adapter may itself be composed of two distinct oligonucleotide molecules that are base paired with each other. As would be apparent, a ligatable end of an adapter may be designed to be compatible with overhangs made by cleavage by a restriction enzyme, or it may have blunt ends or a 5' T overhang. The term "adapter" refers to double-stranded as well as single-stranded molecules. An adapter can be DNA or RNA, or a mixture of the two. An adapter containing RNA may be cleavable by RNase treatment or by alkaline hydrolysis. An adapter may be 15 to 100 bases, e.g., 50 to 70 bases, although adapters outside of this range are envisioned.

The term "adapter-ligated," as used herein, refers to a nucleic acid that has been ligated to an adapter. The adapter can be ligated to a 5' end and/or a 3' end of a nucleic acid molecule. As used herein, the term "adding adapter sequences" refers to the act of adding an adapter sequence to the end of fragments in a sample. This may be done by filling in the ends of the fragments using a polymerase, adding an A tail, and then ligating an adapter comprising a T overhang onto the A-tailed fragments. Adapters are usually ligated to a DNA duplex using a ligase, while with RNA, adapters are covalently or otherwise attached to at least one end of a cDNA duplex preferably in the absence of a ligase. The term "adapter-ligated sample" refers to a sample in which the cfDNA has been ligated to adapters. As would be understood given the definitions above, a sample that has been ligated to an asymmetric adapter contains strands that have non-complementary sequences at the 5' and 3' ends.

The term "asymmetric adapter", as used herein, refers to an adapter that, when ligated to both ends of a double stranded nucleic acid fragment, will lead to a top strand that contains a 5' tag sequence that is not the same as or complementary to the tag sequence at the 3' end. Examples of asymmetric adapters are described in U.S. Pat. Nos. 5,712,126 and 6,372,434 to Weissman et al., and International Patent Publication No. WO 2009/032167 to Bignell et al. An asymmetrically tagged fragment can be amplified by two primers: a first primer that hybridizes to a first tag sequence added to the 3' end of a strand; and a second primer that hybridizes to the complement of a second tag sequence added to the 5' end of a strand. Y-adapters and hairpin adapters (which can be cleaved, after ligation, to produce a "Y-adapter") are examples of asymmetric adapters.

The term "Y-adapter" refers to an adapter that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adapter-tagged double-stranded DNA that has been ligated to a Y-adapter is asymmetrically tagged in that it has the sequence of one strand of the Y-adapter at one end and the other strand of the Y-adapter at the other end. Amplification of nucleic acid molecules that have been joined to Y-adapters at both ends results in an asymmetrically tagged nucleic acid, i.e., a nucleic acid that has a 5' end containing one tag sequence and a 3' end that has another tag sequence.

The term "hairpin adapter" refers to an adapter that is in the form of a hairpin. In one embodiment, after ligation the hairpin loop can be cleaved to produce strands that have non-complementary tags on the ends. In some cases, the loop of a hairpin adapter may contain a uracil residue, and the loop can be cleaved using uracil DNA glycosylase and endonuclease VIII, although other methods are known.

The term "amplifying" as used herein refers to generating one or more copies, or "amplicons," of a template nucleic acid, such as may be carried out using any suitable nucleic acid amplification technique, such as technology, such as PCR (polymerase chain reaction) amplification (including nested PCR and multiplex PCR), RCA (rolling circle amplification), NASBA (nucleic acid sequence-based amplification), TMA (transcript mediated amplification), and SDA (strand displacement amplification). It will be appreciated that a combination of amplification techniques can be advantageously used in certain contexts, e.g., multiplex PCR combined with RCA (see, e.g., Gong et al. (2018) *RSC Adv.* 8:27375), RCA combined with quantitative PCR (qPCR) (see, e.g., Liu et al. (2016) *Anal Sci.* 32: 963-968), and the like.

The terms "enrich" and "enrichment" refer to a partial purification of template molecules that have a certain feature (e.g., nucleic acids that contain 5-hydroxymethylcytosine) from analytes that do not have the feature (e.g., nucleic acids that do not contain 5-hydroxymethylcytosine). Enrichment typically increases the concentration of the analytes that have the feature by at least 2-fold, at least 5-fold or at least 10-fold relative to the analytes that do not have the feature. After enrichment, at least 10%, at least 20%, at least 50%, at least 80% or at least 90% of the analytes in a sample may have the feature used for enrichment. For example, at least 10%, at least 20%, at least 50%, at least 80% or at least 90% of the nucleic acid molecules in an enriched composition may contain a strand having one or more 5-hydroxymethylcytosines that have been modified to contain a capture tag.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" (NGS) or "high-throughput sequencing", as used herein, refer to the so-called parallelized sequencing-by-synthesis or sequencing-by-ligation platforms currently employed by Illumina, Life Technologies, Roche, etc. Next-generation sequencing methods may also include nanopore sequencing methods such as that commercialized by Oxford Nanopore Technologies, electronic detection methods such as Ion Torrent technology commercialized by Life Technologies, and single-molecule fluorescence-based methods such as that commercialized by Pacific Biosciences.

The term "read" as used herein refers to the raw or processed output of sequencing systems, such as massively parallel sequencing. In some embodiments, the output of the methods described herein is reads. In some embodiments, these reads may need to be trimmed, filtered, and aligned, resulting in raw reads, trimmed reads, aligned reads.

A "UFI" is a unique feature identifier that characterizes a group of nucleic acid molecules. A UFI may be a particular sequence of nucleic acids in what is sometimes referred to as a "barcode" (sometimes referred to herein as a "UFI sequence" or "UFI barcode") or it may be a chemical tag as will result from glycosylation, biotinylation, or the like. A UFI may also be the absence of a particular feature such as an appended or incorporated moiety; for instance, a UFI may be the absence of a particular barcode, or the absence of glycosylated or biotinylated moieties, or the like. A UFI sequence is typically a relatively short nucleic acid sequence that serves to identify a feature of a nucleic acid molecule. Nucleic acid template molecules and amplicons thereof that contain a UFI are sometimes referred to herein as "barcoded" template molecules or amplicons. Examples of UFI sequence types include, without limitation, the following:

A "molecular UFI sequence" (or "molecular barcode") is a short sequence of nucleic acids that is appended to every nucleic acid template molecule in a sample, such that, providing the UFI sequence is of sufficient length, every nucleic acid template molecule is attached to a unique UFI sequence. The molecular UFI sequences are usually designed as a string of random nucleotides, partially degenerate nucleotides, or, in some cases, i.e., with a limited number of template molecules, defined nucleotides. Molecular UFI sequences, as is known in the art, can be used to account for and offset amplification and sequencer errors, allow a user to track duplicates and remove them from downstream analysis, enable molecular counting, and, in turn, the determination of an analyte concentration. See, e.g., Casbon et al. (2011) *Nuc. Acids Res.* 39(12):1-8.

A "sample UFI sequence" (or "sample barcode" or "indexed UFI") is a sequence of nucleic acids that is appended to every nucleic acid template molecule in a sample, such that a plurality of samples can be combined, processed, and sequenced together, with the sample UFI sequence enabling the sorting and grouping of reads by sample (i.e., de-multiplexing). A sample UFI sequence identifies the individual from whom the sample was obtained.

A "source identifier sequence" (or "source UFI" or "source barcode") identifies the source of origin. A source UFI will normally be a sample UFI. In certain instances, however, for example when different types of samples are obtained from the same individual (e.g., blood sample, cyst fluid, or the like), a source UFI will indicate the physiological source of the sample rather than the patient from whom the sample was obtained. When multiple samples are combined that include two or more sample types obtained from a single individual, both a sample barcode and a source barcode should be used.

A "fragment identifier sequence" (or "fragment UFI" or "fragment barcode"): In a nucleic acid sample in which nucleic acids comprise a population of many fragments (as occurs naturally in cell-free DNA, or can be engineered through multiple known fragmentation techniques (e.g., physical, sonication, enzymatic, etc.), each fragment in a sample is barcoded with a corresponding fragment identifier sequence. Sequence reads that have non-overlapping fragment identifier sequences represent different original nucleic acid template molecules, while reads that have the same fragment identifier sequences, or substantially overlapping fragment identifier sequences, likely represent fragments of the same template molecule. The unique feature identified here is the template nucleic acid molecule from which a fragment derives.

A "strand identifier sequence" (or "strand UFI" or "strand barcode") independently tags each of the two strands of a DNA duplex, so that the strand from which a read originates can be determined, i.e., as the W strand or the C strand.

A "5hmC identifier sequence" (or "5hmC barcode") identifies DNA fragments originating from 5hmC-containing cell-free DNA template molecules in a sample, i.e., "hydroxymethylated" DNA.

A "5mC identifier sequence" (or "5mC barcode") identifies DNA fragments originating from 5mC-containing cell-free DNA template molecules that do not contain 5hmC.

In some embodiments, a UFI may have a length in the range of from 1 to about 35 nucleotides, e.g., from 2 to 30 nucleotides, 4 to 30 nucleotides, 4 to 24 nucleotides, 4 to 16 nucleotides, 4 to 12 nucleotides, 6 to 20 nucleotides, 6 to 16 nucleotides, 6 to 12 nucleotides, etc. In certain cases, as noted above, the UFI may be error-detecting and/or error-correcting, meaning that even if there is an error (e.g., if the sequence of the molecular barcode is mis-synthesized, misread or distorted during any of the various processing steps leading up to the determination of the molecular barcode sequence) then the code can still be interpreted correctly. The use of error-correcting sequences is described in the literature (e.g., in U.S. Patent Publication Nos. U.S. 2010/0323348 to Hamati et al. and U.S. 2009/0105959 to Braverman et al., both of which are incorporated herein by reference).

The oligonucleotides that serve as UFI sequences herein may be incorporated into DNA molecule using any effective means, where "incorporated into" is used interchangeably herein with "added to" and "appended to," insofar as the UFI can be provided at the end of a DNA molecule, near the end of a DNA molecule, or within a DNA molecule. For example, multiple UFIs can be end-ligated to DNA using a selected ligase, in which case only the final UFI is at the "end" of the molecule.

More generally, the term "detection" is used interchangeably with the terms "determining," "measuring," "evaluating," "assessing," "assaying," and "analyzing," to refer to any form of measurement, and include determining if an element is present or not. These terms include both quantitative and/or qualitative determinations. Assessing may be relative or absolute. "Assessing the presence of" thus includes determining the amount of a moiety present, as well as determining whether it is present or absent. Assessing the level at a hydroxymethylation biomarker locus refers to a determination of the degree of hydroxymethylation at that locus.

"Accuracy" refers to the degree of conformity of a measured or calculated quantity (a test reported value) to its accurate (or true) value. Clinical accuracy relates to the proportion of true outcomes (true positives (TP) or true negatives (TN) versus misclassified outcomes (false positives (FP) or false negatives (FN), and may be stated as a sensitivity, specificity, positive predictive values (PPV) or negative predictive values (NPV), or as a likelihood, or odds ratio, among other measures.

As used herein, the term "correspond to," with reference to a sequence read that "corresponds to" a particular (e.g., the top or bottom) strand of a fragment, refers to a sequence read derived from that strand or an amplification product thereof.

The term "correlate" as used herein in reference to a variable (e.g., a value, a set of values, a disease state, a risk associated with the disease state, or the like) is a measure of the extent to which two or more variables fluctuate together.

A "hydroxymethylation level" or "hydroxymethylation state" is the extent of hydroxymethylation within a hydroxymethylation biomarker locus. The extent of hydroxymethylation is normally measured as hydroxymethylation density, e.g., the ratio of 5hmC residues to total cytosines, both modified and unmodified, within a nucleic acid region. Other measures of hydroxymethylation density are also possible, e.g., the ratio of 5hmC residues to total nucleotides in a nucleic acid region.

A "hydroxymethylation profile" or "hydroxymethylation signature" refers to a data set that comprises the hydroxymethylation level at each of a plurality of hydroxymethylation biomarker loci. The hydroxymethylation profile may be a reference hydroxymethylation profile that comprises composite hydroxymethylation profile for a population of individuals with at least one shared characteristic, e.g., individuals who have never been diagnosed with cancer, individuals who have never had a lesion identified in an imaging scan, individuals over 65, female individuals, and the like. A hydroxymethylation profile may include the density, location, relative positioning and/or pattern of 5-hydroxymethylcytosines in a nucleic acid, nucleic acid fragment, or nucleic acid region.

A "formula," "algorithm," or "model" is any mathematical equation, algorithmic, analytical or programmed process, or statistical technique that takes one or more continuous or categorical inputs and calculates an output value, sometimes referred to as an "index," "index value," "predictor," "predictive value," "probability," or "probability score." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. In panel and combination construction, of particular interest are structural and syntactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Many such algorithmic techniques have been further implemented to perform both feature (loci) selection and regularization, such as in ridge regression, lasso, and elastic net, among others. Other techniques may be used in survival and time to event hazard analysis, including Cox, Weibull, Kaplan-Meier and Greenwood models well known to those of skill in the art. Many of these techniques are useful either combined with a hydroxymethylation biomarker selection technique, such as forward selection, backwards selection, or stepwise selection, complete enumeration of all potential biomarker sets, or panels, of a given size, genetic algorithms, or they may themselves include biomarker selection methodologies. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art.

Algorithms of various types are used herein to derive meaningful sets, such as a group of genes that are more commonly represented, or more commonly represented and more commonly expressed, in a particular tissue type. The same or different algorithms are also used to determine a statistical correlation between two or more data sets, such as one or more standard, or "normal," hydroxymethylation profiles and a hydroxymethylation profile from a patient sample. Regression analysis is the common statistical technique that serves as the basis of several comparative algorithms; examples of commonly used regression models include Ridge, Lasso, and Elastic Net. Simple linear regression (ordinary least squares, or "OLS") is generally insufficient because of relatedness between variables; instead, a penalty is added to account for and offset relatedness, either L1 regularization (Lasso regression), L2 regularization (ridge regression) or both. The glmnet model (Lasso and Elastic Net-regularized generalized linear model) provides a default optimized fit that varies both penalty weight and the L1 and L2 contributions; when the optimal fit weighs L2 preferentially, the predictor will tend to be supported by a large number of features. Glmnet2 refers to a lasso fit in which only L1 contributes to the penalty, typically resulting in a sparse model supported by a small number of features. Elastic Net incorporates penalties from both L1 and L2 regularization, with the ratio of the L1 and L2 terms optimized. An exemplary technique herein, sometimes referred to herein as glmnet1A, involves use of a modified glmnet model where L1 and L2 are weighted in a 55/45 ratio.

2. Tissue of Origin Assignment

In one embodiment, a method is provided for probabilistically assigning a tissue of origin to a nucleic acid in a cell-free fluid sample obtained from a human subject, where "probabilistic" assignment of a tissue of origin involves determination of a probability that the nucleic acid originates from a specific tissue. The tissue of origin is the tissue source of the nucleic acid, where the term "tissue" is used to describe a group or population of cells of the same type and, if associated with an organ, the same organ. That is, given a cell-free fluid sample from a human subject containing a nucleic acid such as DNA from an unknown tissue, the present method can be used to generate data that is tissue-specific and enables a probabilistic assignment of tissue of origin to the sample DNA. The method involves the generation of a hydroxymethylation profile for a sample nucleic acid followed by a comparison of that hydroxymethylation profile with each of a plurality of reference hydroxymethylation profiles in a reference data set, each reference hydroxymethylation profile corresponding to a reference locus contained within a genomic region associated with a tissue-specific gene. The genomic regions containing the reference loci are differentially hydroxymethylated regions (DhMRs), which essentially serve as biomarkers herein, and are selected as having hydroxymethylation profiles that tend to vary with particular tissue of origin, tissue type, tissue condition, and other factors. Each reference hydroxymethylation profile is contained within a hydroxymethylation vector having the following information for a specific reference locus, or biomarker: a normal, or control hydroxymethylation profile at the specific reference locus; the tissue-specific gene associated with the reference locus; and the tissue with which the gene and reference locus are associated.

(a) Detection of Hydroxymethylation Profile:

The first step of the method involves detecting the hydroxymethylation profile of a nucleic acid in a sample, typically a cell-free DNA sample obtained from a human subject, wherein the "nucleic acid" may be one or more nucleic acid molecules, nucleic acid fragments, or nucleic acid regions, or a combination thereof, and the "hydroxymethylation profile" can be hydroxymethylation density, e.g., the ratio of 5hmC residues to total cytosines, both modified and unmodified, within a nucleic acid region. Other measures of 5hmC density are also envisioned, e.g., the ratio of 5hmC residues to total nucleotides in a locus, and other types of evaluations may also be useful, e.g., the ratio of 5hmC to 5mC within a locus.

In addition to 5hmC density, the hydroxymethylation profile may also comprise hydroxymethylation information such as hydroxymethylation pattern, total 5hmC residues within a nucleic acid region, the location of 5hmC residues within a nucleic acid region, the relative positions of 5hmC residues within a nucleic acid region, and/or identification of a hydroxymethylated site as hemi-hydroxymethylated or fully hydroxymethylated. As 5hmC has been recently identified as a key epigenetic modification that has a fundamental role in the epigenetic regulation of mammalian systems, researchers have worked on developing techniques for ascertaining hydroxymethylation profiles of nucleic acids, nucleic acid fragments, and nucleic acid regions, i.e., loci within a nucleic acid or fragment.

A preferred method for detecting the hydroxymethylation profile of a nucleic acid is described in International Patent Publication WO 2017/176630 to Quake et al., incorporated herein by reference in its entirety. That method pertains to the detection of 5-hydroxymethylcytosine patterns in cell-free DNA within the context of a sequencing scheme. An affinity tag is appended to 5hmC residues in a sample of cell-free DNA, and the tagged DNA molecules are then enriched and sequenced, with 5hmC locations identified. An illustrative example of the method, as described in Quake et al., involves initially modifying end-blunted, adaptor-ligated double-stranded DNA fragments in the cell-free sample to covalently attach biotin, as the affinity tag, to 5hmC residues. This may be carried out by selectively glucosylating 5hmC residues with uridine diphospho (UDP) glucose functionalized at the 6-position with an azide moiety, a step that is followed by a spontaneous 1,3-cycloaddition reaction with alkyne-functionalized biotin via a "click chemistry" reaction. The DNA fragments containing these biotinylated 5hmC residues can then be pulled down with streptavidin beads in the "enrichment" step.

The enriched DNA sample can be amplified using one or more primers that hybridize to the added adaptors or to their complements. In embodiments in which Y-adaptors are added, the adaptor-ligated nucleic acids may be amplified by PCR using two primers: a first primer that hybridizes to the single-stranded region of the top strand of the adaptor, and a second primer that hybridizes to the complement of the single-stranded region of the bottom strand of the Y adaptor (or hairpin adaptor, after cleavage of the loop). For example, in some embodiments the Y adaptor used may have P5 and P7 arms (which sequences are compatible with Illumina's sequencing platform) and the amplification products will have the P5 sequence at one and the P7 sequence at the other. These amplification products can be hybridized to an Illumina sequencing substrate and sequenced. In another embodiment, the pair of primers used for amplification may have 3' ends that hybridize to the Y adaptor and 5' tails that either have the P5 sequence or the P7 sequence. In these embodiment, the amplification products will also have the P5 sequence at one and the P7 sequence at the other. These amplification products can be hybridized to an Illumina sequencing substrate and sequenced. This amplification step may be done by limited cycle PCR (e.g., 5-20 cycles).

The sequencing step may be done using any convenient next generation sequencing method and may result in at least 10,000, at least 50,000, at least 100,000, at least 500,000, at least 1M, at least 10M, at least 25M, at least 50M, at least 100M or at least 1B sequence reads. In many cases, the reads are paired-end reads. The primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform, or Pacific Biosciences' fluorescent base-cleavage method. Examples of such methods are described in the following references: Margulies et al. (2005) *Nature* 437: 376-80; Ronaghi et al. (1996) *Analytical Biochemistry* 242: 84-9; Shendure (2005) *Science* 309:1728); Imelfort et al. (2009) *Brief Bioinform.* 10:609-18; Fox et al. (2009) *Methods Mol Biol.* 553:79-108; Appleby et al. (2009) *Methods Mol Biol.* 513:19-39; English (PLoS One. 2012 7: e47768) and Morozova (2008) *Genomics* 92:255-64), which are incorporated by reference for the general descriptions of the methods and the particular steps of the methods, including all starting products, reagents, and final products for each of the steps.

In certain embodiments, the sample sequenced may comprise a pool of DNA molecules from a plurality of samples, wherein the nucleic acids in the sample have a molecular barcode to indicate their source. In some embodiments the nucleic acids being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.). As such, in certain embodiments, a cell-free nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

The sequence reads may be analyzed by a computer and, as such, instructions for performing the steps set forth below may be set forth as programming that may be recorded in a suitable physical computer readable storage medium.

In some embodiments, the sequence reads may be analyzed to provide a quantitative determination of which sequences are hydroxymethylated in the cfDNA. This may be done by, e.g., counting sequence reads or, alternatively, counting the number of original starting molecules, prior to amplification, based on their fragmentation breakpoint and/or whether they contain the same indexer sequence. The use of molecular barcodes in conjunction with other features of the fragments (e.g., the end sequences of the fragments, which define the breakpoints) to distinguish between the fragments is known. Molecular barcodes and exemplary methods for counting individual molecules are described in Casbon (2011) *Nucl. Acids Res.* 22 e81 and Fu et al. (2011)

*Proc. Natl. Acad. Sci. USA* 108: 9026-31), among others. Molecular barcodes are described in U.S. Patent Publication Nos. 2015/0044687, 2015/0024950, and 2014/0227705, and in U.S. Pat. Nos. 8,835,358 and 7,537,897, as well as a variety of other publications.

The sequenced nucleic acid with 5hmC locations identified provides the information needed as to the hydroxymethylation profile of that nucleic acid.

Other methods of ascertaining the hydroxymethylation profile of DNA in a cell-free sample are described in Provisional U.S. Patent application Ser. No. 62/630,798 to Arensdorf for "Methods for the Epigenetic Analysis of DNA, particularly Cell-Free DNA," filed Feb. 14, 2018, and in U.S. Patent Publication No. 2017/0298422 to Song et al., both of which are incorporated by reference herein. These references are also useful in conjunction with an embodiment of the invention in which the present method further includes the detection of a sample DNA methylation profile and its use in an expanded comparison, wherein in addition to the hydroxymethylation analysis, methylation profiles are compared as well, using a reference set of methylation profiles analogous to the hydroxymethylation profile reference set. That is, the references describe the generation of a methylation profile and a hydroxymethylation profile from a single DNA sample.

(b) The Reference Data Set:

Following the generation of the hydroxymethylation profile of a sample nucleic, that detected hydroxymethylation profile is compared with each of a plurality of reference hydroxymethylation profiles in a reference data set, where each reference hydroxymethylation profile is associated with a reference locus associated with a tissue-specific gene. In a preferred embodiment, the reference set is a large hydroxymethylome data set, containing hydroxymethylation vectors for each of a plurality of reference loci associated with each of a plurality of tissue-specific genes. That is, the hydroxymethylome data set may contain information for at least three, at least five, at least 10, or at least 30 tissue types, with, typically, at least three genes per tissue type, or at least 10, at least 20, at least 25, or more genes per tissue type. The hydroxymethylation vector, for each reference locus, contains at least the following information: the identification of the reference locus; the tissue-specific gene associated with the locus; the tissue of origin corresponding to the tissue-specific gene; and the hydroxymethylation profile. The hydroxymethylation profile as noted earlier includes the hydroxymethylation density within the reference locus as well as other items of information, such as total 5hmC residues within the locus, location of 5hmC residues within the locus, relative positions of 5hmC residues within the locus, and identification of a hydroxymethylated site as hemi-hydroxymethylated or fully hydroxymethylated.

The reference loci may be contained with a gene body or a component thereof, such as within an intron or exon. The reference loci may also be contained within a genomic annotation feature outside of the gene body, such as a promoter, an enhancer, a transcription initiation site, a transcription stop site, a DNA binding site, or a combination thereof. DNA binding sites that may contain one or more reference loci include, by way of example, silenced regions, transcription factor binding sites, transcription repressor binding sites, and CTCF binding sites (transposon repeat regions). Reference loci within CTCF binding sites are of particular interest, insofar as the CTCF gene codes for transcriptional repressor CTCF (also known as 11-zinc finger protein or CCCTC-binding factor), which in turn is involved in many cellular processes, including transcription regulation and regulation of chromatin architecture. See, for example, Juan et al. (2016) *Cell Reports* 14(5): 1246-1257; and Escedi et al. (2018) *Epigenomes* 2(1):3.

Accordingly, each reference hydroxymethylation profile in the reference data set corresponds to a reference locus associated with at least one gene originating from a particular tissue type. In one embodiment, each reference hydroxymethylation profile in the reference set corresponds to a reference locus associated with at least one gene originating from a human tissue type (or functional, organ, anatomical and related cell-lineage groupings of types, e.g. digestive, brain and myeloid- or lymphoid-derived) including: adipose; adrenal gland; bone marrow; brain; breast; colon; cerebral cortex; cervical; uterine; digestive; endometrial; epididymal; esophageal; Fallopian tube; gall bladder; heart muscle; hypothalamus; kidney; liver; lung; lymph nodes; ovary; pancreas; parathyroid gland; placenta; prostate; salivary; seminal vesicle; skeletal muscle; smooth muscle; skin; spleen; stomach; testis; thyroid gland; tonsil; bladder; and combinations thereof. The foregoing list is merely illustrative and is not intending to be limiting.

Many human tissues, including those enumerated above, are comprised of two or more sub-types, and the foregoing list is intended to include any and all such subtypes. For instance, adipose tissue may be brown adipose tissue (BAT) or white adipose tissue (WAT), and if white adipose tissue, either subcutaneous white adipose tissue (SWAT) or intra-abdominal visceral white adipose tissue (VWAT); see Gil et al. (2011) *Int. J. Pediatr. Obes.* 6 Suppl. 1:13-20. Adrenal tissue may be from the adrenal medulla or the cortex. Bone marrow includes myeloid tissue, i.e., red bone marrow, and fatty tissue, or yellow bone marrow, and the present methodology is potentially useful in distinguishing myeloid-derived lineages of blood cells and lymphoid-derived lineages of blood cells.

Digestive tissue comprises all four of the major tissue types, epithelial, connective, muscle, and neural, including the connective tissue of the submucosa, the striated muscle tissue of the esophagus, and goblet cell tissue, the mucus-secreting epithelial cells that line the entire digestive tract. Many additional tissue subtypes are known in the art and/or can be readily identified by reference to the pertinent texts and literature.

The tissue-specific genes with which the reference loci are associated are genes that are correlated with a particular tissue, with varying degrees of correlation or specificity. Certain genes have similar hydroxymethylation profiles in all cells (i.e., house-keeping genes), while others have differentially represented hydroxymethylation patterns in various tissues throughout the human body. Reference loci associated with differentially represented genes are of primary interest herein, insofar as hydroxymethylation patterns associated with genes that are highly represented in a particular tissue are most useful in a tissue determination. Of further interest are those differentially represented hydroxymethylated genes where such representation correlates with gene expression levels that also have a specificity to particular tissues, being differentially expressed in said tissue to varying degrees of correlation or specificity. Information concerning differentially expressed genes will be known to those skilled in the art and is provided in the relevant texts and literature; numerous gene-tissue expression databases are also available. See, e.g., the "human tissue proteome" in the Human Protein Atlas at www.p-reoteinatlas.org; also see Uhlen et al. (2015), "Tissue-based map of the human proteome," *Science* 347(6220). The Human Protein Atlas categorizes tissue-specific genes according to the ratio of mRNA level observed in a particular tissue relative to other tissues, with "tissue enriched" genes that share expression in a limited number of tissues and exhibit at least five-fold higher mRNA levels relative to all other tissues, "group enriched" genes exhibiting at least five-fold higher mRNA levels relative to 2-7 other genes within a gene group, and "tissue enhanced" genes exhibiting at least five-fold higher mRNA levels in a particular tissue relative to average levels in all tissues.

Examples of tissue-specific genes are provided in sections (c), (d), and (e) below. The genes in section (c), Set 1, were identified by analysis of 17 tissue types from each of five individuals. For identification of differentially represented tissue-specific genes, processing was carried out using the "5hmC Seal" technique of Song et al. (2011) *Nature Biotechnology* 29: 68-72. For identification of the differentially represented, differentially expressed tissue-specific genes in section (d), Set 2, further processing was carried out using RNAseq. Log-CPM transformations were carried out and analyzed with respect to both (1) the difference in log-CPM between a tissue of interest and the maximum value across all other tissues, and (2) the ratio of the log-CPM obtained for the tissue of interest and the maximum value across all other tissues. The tissue-specific genes in section (e), Set 3, were identified using 19 tissue types from multiple individuals (sigmoid and transverse colon, 6 donor samples; hypothalamus, 4 donor samples; and all other tissues, 5 donor samples each) and analyzed the glmnet1A methodology explained earlier herein.

(c) Differentially Represented Tissue-Specific Genes—Set 1:

As explained previously, the tissue-specific genes with which the reference loci are associated are differentially represented, so that a tissue or cell sample of unknown origin can be identified by comparison with reference hydroxymethylation profiles for known tissues, where "identified" refers to the probabilistic assignment of a tissue of origin, to, e.g., a nucleic acid in a cell-free fluid sample. A first set of differentially represented genes was identified using the aforementioned methodology, i.e., RNAseq followed by log-CPM transformation and comparison. The genes of Set 1 are particularly useful in a reference set for probabilistically assigning a tissue of origin to a tissue or cell sample of unknown origin.

Set 1:

Bladder: AARD, ADARB1, AKR1B10, ANAPC7, APCDD1L-AS1, APOA1BP, CALHM2, CASC3, CLEC2L, COL4A5, CRYM-AS1, EPHA3, FAHD2B, FKBP9L, FOPNL, GNG11, GSN, GSTTP2, GTSF1, IAH1, KCNMB1, KIAA1644, LAMC1, LINC00310, LOC100506394, LOC100507066, LOC493754, MAP1B, MGC27382, MIR5695, NENF, NT5DC3, P2RX1, PCP4, PGM5, PLCD4, PTGFR, RBFOX3, RPL30, SCARA3, SLIT3, SNX29P1, SPATA4, ST8SIA1, TBX4, TXNRD1, VCL, VPS72, WFDC3, and ZNF791.

Bone marrow: ADAMTS20, AFF2, ANKRD18B, ANKRD18DP, ANKRD20A5P, ANKRD20A8P, ANKRD26P1, ANKRD30BP2, ANKRD34B, ANKRD34C, ATP6V0B, AVPR1A, BLOC1S3, BOLL, BRIP1, C5orf63, CA1, CALB1, CALCR, CCDC39, CCDC96, CDCA5, CDH12, CDH9, CEACAM8, CENPE, CENPK, CFL1, CHAT, COMMD5, COMMD8, CRISP1, CRISP2, CSN1S1, CSN1S2AP, CT64, CXCR2, CXorf30, DAZL, DCDC1, DRGX, DSG1, DUT, DUX2, DUX4L2, DUX4L3, DYTN, EDA2R, EFCAB3, EPOR, EVX2, F13A1, FCAR, FCER1A, FKBP1B, FOXA2, GABPB1-AS1, GABRA1, GABRA4, GABRG1, GALNTL6, GFER, GFI1, GPR152, GPR158-AS1, GPRC6A, GRM1, GRP, GRXCR1, GYPA, HAGHL, HCRTR2, HEPHL1, HJURP, HK3, HMBS, HORMAD2, ID4, IL17RA, IL18RAP, KCNC2, KCNK18, KIF18A, KIF20B, KLHL1, LEF1-AS1, LHX1, LHX3, LHX8, LINC00273, LINC00558, LINC00645, LINC00648, LLPH, LOC100129620, LOC100270679, LOC100505776, LOC100506422, LOC284801, LOC392232, LOC399815, LOC401074, LOC401134, LOC440040, LOC440970, LOC642236, LOC727924, LOC728012, LPO, LRRIQ1, MAGEA11, MAGOHB, MEFV, MIF4GD, MIR548A3, MIR5692A1, MMP8, MMP9, MMRN1, MRGPRE, MS4A3, MSRB1, MYO3A, NCOR1P1, NDST3, NDST4, NHLRC4, NOXRED1, NPAP1, NUF2, OR8G1, OR8U8, ORC6, OSM, OTX2, PAX3, PBK, PCDH8, PDCL2, POTEA, PROK2, PRR7, RAB24, RAX, RBM46, RGS18, RGS19, RIMS2, RNF175, RRM2, SATB2-AS1, SCN11A, SCRT2, SERPINB10, SGOL2, SIX1, SKA3, SKOR1, SLC22A16, SLC4A10, SLC5A7, SLC5A8, SLCO6A1, SNAP91, SPAG16, SPATA16, SPDL1, SPINK13, STPG2, STXBP5L, TARM1, TDRD5, TEX15, THSD7B, TMPRSS11A, TMPRSS11B, TMPRSS11D, TRIM58, TUBB4B, UNC13C, USP6, VRK1, VSTM1, VWDE, WDR49, WFDC8, WFDC9, ZIC5, ZNF230, ZNF300P1, ZNF470, ZNF502, ZNF599, and ZPBP.

Brain tissue: Clorf159, CCDC42B, CCDC8, CD248, CERCAM, CNTN2, CRB2, EVI5L, FZD9, HAPLN2, HPDL, LINC00575, LOC284950, LOC339666, LRIT1, PLEKHH1, SHISA2, SLC46A2, TFAP2E, TMEM235, TNFRSF18, and ZFP36.

Colon: Clorf109, CACNA1F, COX7B, EFNB1, FGL2, F1134208, GNRH1, GSTT1, IL12A, KCND1, KDELR1, LAT, LOC100130992, LOC100287042, LOC401242, MRPL10, NT5C3B, PDZD4, PPYR1, RAD51D, RBMXL3, RENBP, SCNN1B, SERPINB5 SLC9A6, XBP1, and ZNF189.

Heart muscle tissue: ABR, ADPRHL1, ASB18, ATP1A3, CCDC74A, CDH13, CHRNA10, CORO6, FSD2, GALNT16, GDAP1L1, GJA3, GLUD1P3, GPRC5B, LOC100506343, LRRC37A6P, LRRC4, MUL1, MYOM2, NDUFB8, NT5DC2, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PXDNL, RHPN1-AS1, RPL3L, SGCG, TIMM21, TNNT1, TOR4A, UBAC1, WDR37, ZNF12, ZNF213, ZNF550, ZNF843, and ZNF844.

Hypothalamus: AGAP6, ASTN1, BBS2, C18orf56, C19orf45, CINP, DGKI, DPY30, DROSHA, FAM169A, FAM66D, FONG, GALNT15, GDAP1, GHRH, GUSBP4, HIF1AN, IFIT1B, INTS2, JAKMIP2-AS1, KGFLP2, LINC00297, LINC00707, LOC100288069, LOC100507140, LPHN3, LYPD1, LZIC, MIR548T, MRAP, NTRK3, PDE6D, PPP1R17, PRSS54, PRSS55, PTPRA, RGS7, SNRNP35, SUGT1P1, UBE2Z, WDR47, WDYHV1, ZNF114, ZNF556, and ZNF610.

Kidney: ABP1, AGPAT9, APH1B, ASAP2, ATP4B, ATP6V1A, BBOX1, BCRP3, C11orf63, C13orf35, C16orf96, C19orf21, CA12, CCDC64, COL4A3, CXCL14, CYS1, EIF4E2, EPB41L1, EVC, FIGNL2, FUT3, GALNT14, GLIS2, GUSBP11, HAVCR1, HOXC5, INADL, KATNA1, L2HGDH, LOC100130238, LOC100506305, LOC284100, LOC654433, LYG1, MORN4, MTNR1A, PAQR5, PARG, PAX2, PAX8, PLA2G15, POU5F1, PRKAB1, RNF113B, SENP8, SETD3, SLC22A2, SLC25A30, SLC9A3, SULT1C2, TBC1D7, and TSPAN33.

Liver: ABCB4, ABCC11, ABCC2, ABCG5, ABCG8, ACADSB, ACSM5, AGMO, AGXT2L1, AKR1C2, AKR1C4, AKR1D1, AMDHD1, APOB, APOH, APOM, AQP9, ARHGEF40, ASGR2, ASPG, ATP2B2, BCO2, BDH1, C3, C3P1, C5, C8A, C8B, C8orf74, CASA, CABP2, CALR3, CD7, CDK10, CEACAM16, CES1, CFH, CFHR4, CHP1, CIDEB, CLPTM1L, CLRN3, CPN2, CREB3L3, CROCCP2, CYP2B6, CYP2C18, CYP2C19, CYP2C9, CYP2E1, CYP3A5, CYP7A1, DGAT2, DHODH, DPYS, DRG2, ECHS1, EDC4, EI24, ENO1, F13B, F2, F7, F9, FASN, FETUB, GCH1, GCKR, GDPD4, GFRA1, GHR, GLT1D1, GPAM, GSDMB, HAL, HAO1, HAPLN4, HPD, HPX, HYLS1, IGF2, IGF2-AS, IGFBP1, ISY1-RAB43, ITIH1, ITIH2, ITIH4, IVD, KLC4, LBP, LEFTY1, LIPG, LOC100288122, LOC284865, LPAL2, LRRC16B, MASP1, MGMT, MST1, MTTP, NAT9, NBR2, NELFE, NR1I2, NUP88, OSGIN1, PAH, PARD6A, PCSK9, PEX19, PGLYRP2, PHGDH, PHYH, PKLR, PLA2G12B, PLG, PNPLA3, POFUT1, POLR1E, PON1, PPL, PRAP1, PRKAG3, PROC, PUSS, RANBP10, RCE1, RND1, RNF123, RORC, RPUSD4, SAA2-SAA4, SCP2, SEC16B, SERPINA6, SERPINC1, SKIV2L, SLC13A5, SLC22A25, SLC25A20, SLC27A5, SLC30A10, SLCO1B3, SMLR1, SNAPC5, SPP2, SRD5A1, STAT2, STEAP3, SULT2A1, TFR2, THNSL2, TIAF1, TM6SF2, TMEM45A, TMPRSS6, TTC31, TTC38, UROC1, XYLB, ZCCHC9, and ZSCAN22.

Lung: ADAMS, ANKRD50, ARGLU1, ARL6, ARSJ, BMP5, BMPR2, BTG3, Clorf140, CALM2, CCDC102B, CCNL1, CCR5, CD36, CHN1, CLIC2, CPEB2, CRBN, CYP4Z2P, CYYR1, DACH1, DGKE, DGKH, DISP1, DOCK4, ETV1, EXOC1, FAM204A, FAT4, FGD5-AS1, FLJ34503, FRYL, GBP1P1, GNB4, GPR110, GPR116, HMCN1, HMGN1, IFI44, IL15, ITGA2, KAL1, KDR, KITLG, KLHL41, LDB2, LINC00032, LINC00240, LINC00551, LINC00657, LOC100131234, LOC100505495, LOC100507217, LOC643733, LPAR6, MGP, ODF2L, PEAK1, PKIA, PLEKHA1, PLEKHG7, PTPRB, QKI, RAD21, RALA, RAP2A, RCC1, SAMD12, SESTD1, SH3GLB1, SKAP2, SLC35A5, SMURF2, SPRED1, SRSF1, TCF4, TIGD4, TMEM207, TMOD3, UHMK1, VEGFC, XIST, YIPF5, ZC2HC1A, and ZEB1.

Lymph nodes: AKNA, ANKRD34A, C14orf183, CCDC107, CD180, CD3G, CD74, CDC42SE2, CHMP7, COTL1, CYTH1, FAIM3, FAM65B, GPX4, GSTP1, HLA-DMA, HLA-DOA, HLA-DPB1, HVCN1, ICAM2, ICOS, IL6, ITGB7, LOC100130557, MDM4, METTL21D, MGC16275, MIR548AN, NAPSB, RPL39L, RPS11, SEPT6, SH2D3C, TAP1, TEAD2, TMEM60, TNFRSF9, TRAF1, UBAC2, UCP2, and WDR87.

Ovarian tissue: ACTA2, ADAMTS5, AQP11, ATP1B2, BICD1, C7, CDH3, CDON, COL14A1, HS3ST1, KLF4, LEMD1-AS1, LINC00672, LOC100129617, LOC339298, LRRC17, NDP, NTF3, OMD, PDGFRA, PGR, ROBO4, RWDD4, SCD5, SERPINE2, SLC25A17, SNCAIP, SYTL4, TENM4, TSPAN5, UBXN8, and ZNF93.

Pancreas: ALDH1L2, ANKEF1, ASUN, B3GALNT2, BBIP1, C6orf201, CASP9, CCDC110, CCDC65, CDK14, CELA2B, CELA3B, CFTR, CHMP4C, CHRNA7, CLCN3, CLDN1, CPA3, CUZD1, DNAJC10, DNAJC3, EIF2S1, EIF4EBP1, ERO1LB, FAIM, FAM160A1, FAM162A, FAM221A, FAM24B-CUZD1, GARS, GUCA1C, HSPA13, IFRD1, INTS6, KCTD16, LINC00339, LMAN1, LOC154092, LOC201651, LOC644838, LYPD6B, MAN1A2, MGC72080, MKNK1, MPP6, MSRB2, NAA16, NOMO2, OSTC, PEX7, PGRMC2, PIK3CB, PLA2G12A, PM20D1, PPP1R9A, PRRC1, PRSS3, RNPC3, SCFD1, SCRN3, SERPINI2, SH3YL1, SLC16A7, SLC33A1, SLC4A4, SORBS2, SRBD1, SSR1, TDH, TDP2, TMEM51-AS1, TMEM65, TRHDE, TRIM44, UGT2A3, UMOD, WDFY2, WHAMM, and XPOT.

Placenta: ACER2, ADAM12, ADCY10, ADCY7, ADORA2B, AIM1L, AKNAD1, ALDH3B2, AMOT, ANGPT2, APOLD1, ATF3, ATG9B, ATP6V1C2, ATRIP, BCAR3, BCAR4, BEAN1, BPGM, BTBD19, C11orf70, C16orf46, C16orf74, C17orf98, C1QTNF6, C2orf62, C2orf83, C3orf52, C4orf26, C4orf51, C6orf99, C7orf71, C9orf129, CACNA2D3-AS1, CAPN6, CCDC125, CEP41, CLEC7A, CPA4, CSF3R, CTSL3P, CXorf56, CYP19A1, DACT2, DDX59, DLX3, DLX5, DLX6-AS1, DNMT1, DUSP4, EBI3, EDARADD, EPAS1, EPS8L1, ERVFRD-1, ERVMER34-1, ETV3, ETV4, EXTL1, EZR, FAM184A, FAM89A, FANCE, FBLN1, FBN2, FHDC1, FOLR1, GATA2, GATA3, GBA, GCM1, GDPD3, GLDN, GM2A, GPR156, GSG1, GSTA3, GSTA4, HELLS, HOPX, HSD11B2, HSPBAP1, IGF2BP3, IGSF5, ISM2, KATNBL1, KIAA1467, KIAA1609, KISS1, KLRG2, L1TD1, LCMT1, LCTL, LIN28B, LINC00439, LOC100131564, LOC100506746, LOC100527964, LOC151475, LOC152578, LOC284551, LOC643441, MB21D2, MED12, METTL21C, MFSD2B, MGC16121, MINA, MORC4, MSANTD3, MUTYH, NOS3, NVL, NXF1, OLR1, OSCP1, OSTCP1, P2RY6, PCBP1-AS1, PDE6A, PGC, PGF, PLA1A, PLAC4, PPP1R14D, PSG11, PSG2, PSG6, PSG7, PSG8, PTGES, PVRL3-AS1, PVRL4, PWWP2B, RAB36, RHO, RNF222, RPSAP58, RS1, SBF2-AS1, SCIN, SDC1, SEMA3F, SEMA6D, SEPT12, SH2D7, SH3GLB2, SLC13A4, SLC26A2, SLC2A1-AS1, SMAGP, SMARCB1, SMIM13, SNX12, SP6, SPESP1, SPIRE2, ST3GAL6-AS1, SVEP1, SYT8, TENM3, TLR3, TMEM216, TMEM218, TMEM52B, TMPRSS7, TP63, TPRXL, TRIM29, TRPV5, TUFT1, USHBP1, VAMPS, VGLL1, WBP2NL, XRCC2, ZDHHC1, ZNF320, ZNF331, ZNF354B, ZNF468, ZNF525, ZNF702P, ZNF90, ZP3, ZSWIM2, and ZSWIM7.

Prostate tissue: ABCC4, ACPP, ALDH1A2, ANKRD66, AP1B1P1, ARG2, BEND4, C1orf85, C6orf132, C6orf52, CHRNA2, COQ7, EVX1, EYA2, F1139080, GDEP, HMGN2P46, ISX, KLKP1, MCCC2, MEAF6, MFSD4, MRPS23, NCAPD3, OACYLP, OAZ3, OR51E2, PAK1IP1, PCAT1, PI15, PPP1R7, PSMA4, SCNN1G, SLC14A1, SLC26A3, SLC2A12, SLC30A4, SLC35F2, TMEM79, TPM3P9, TTC12, USP50, ZNF350, ZNF532, and ZNF589.

Smooth muscle tissue: AKIP1, ARHGEF26-AS1, ATG4A, BOLAS, CHMP4A, DHH, EPPK1, FCHSD1, GADL1, GCC1, GIPC3, HIGD2B, HTR3C, LINC00654, LOC91948, OLFML3, PTGES3L, WSCD2, ZNF202, ZNF205-AS1, and ZNF426.

Stomach: ACOT1, C12orf54, CREB3, DDN, FAM50A, FNDC4, GORASP1, GUCA1B, IMPDH2, LINC00284, LOC100128076, LOC100128682, LOC100131434, LRP10, LRRC55, LRRC73, NOTO, RNF112, RTBDN, SIGLEC8, TNN, TRIM50, UBE2T, ZNF391, and ZNF792.

Testis: ALX4, AQP2, ATAD3B, C11orf85, CABLES2, CCDC114, CCDC27, CCNF, CD300C, CILP, DES, DMRT1, DNAJB8-AS1, DRD4, EFCAB6-AS1, FAM153B, FAM163B, FGD2, HSD17B3, IFI27L1, IGFN1, ITPR3, KCNK15, KIFC2, KRT78, KRT82, LOC100506385, LOC283914, LOC284661, LOC399829, LOC653712, LOC728716, MAGED2, MYH16, MYLK2, NPTX2, PLK5, PMS2CL, PNPLA1, PODNL1, POLD1, PRMT8, PTPRVP, RD3, RIMS4, RNU6-81, RPL26L1, SALL4, SERPINA10, SPATA31E1, STAB1, SULT4A1, TCERG1L, TEKT4P2, THEG, TMEM130, TPO, UPK3B, WASH3P, WRAP53, ZNF280B, and ZNF793.

(d) Differentially Represented, Differentially Expressed Tissue-Specific Genes—Set 2:

In some embodiments, the tissue-specific genes with which the reference loci are associated are differentially represented as well as differentially expressed. These genes are also useful in probabilistically assigning a tissue of origin to a tissue or cell sample of unknown origin, as may be the case in a cell-free fluid sample obtained from a human subject. Representative differentially represented, differentially expressed tissue-specific genes, Set 2, are as follows:

Bladder: AARD, ADARB1, AKR1B10, CRYM-AS1, EPHA3, GTSF1, KCNMB1, MAP1B, NT5DC3, P2RX1, PCP4, PGM5, PLCD4, PTGFR, RBFOX3, SCARA3, SLIT5, SNX29P1, ST8SIA1, TBX4, TXNRD1, VCL, and WFDC3.

Bone marrow: ABCA13, AZU1, CA1, CEACAM8, CLEC6A, DAZL, DRGX, DYTN, ELANE, FCAR, GFI1, GYPA, HK3, IL18RAP, LINC00333, LINC00550, LINC00558, LIPN, LOC100129620, LOC442028, LPO, MEFV, MMP8, MMP9, MPO, MS4A3, MYB, MYO1F, NCOR1P1, NME8, OR8U8, OSCAR, PARPBP, PAX3, PDCL2, PRDM13, PROK2, RGS18, RGS21, RRM2, RXFP2, SERPINB10, SLC22A16, SPATA16, SPI1, SPTA1, TARM1, TMPRSS15, TRIM58, VSTM1, and XKR3.

Brain tissue: ASPHD1, BRSK1, CCDC177, CNTN2, HAPLN2, KCNJ10, KIF1A, LGI3, NCAN, NR2E1, RHBDL3, TMEM151A, TMEM235, TMEM59L, and ZNF488.

Colon: FGL2 and SCNN1B.

Heart muscle tissue: ADPRHL1, ASB18, ATP1A3, CDH13, CORO6, FSD2, GALNT16, GJA3, MYOM2, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB5, PCDHGB6, PCDHGB7, PXDNL, RPL3L, SGCG, and TNNT1.

Hypothalamus: ASTN1 and DGK1.

Kidney: BBOX1, BCRP3, CA12, COL4A3, CXCL14, CYS1, EVC, FIGNL2, GALNT14, GLIS2, HAVCR1, LOC100130238, PAQR5, PAX2, PAX8, PLA2G15, SLC22A2, SLC9A3, SULT1C2, and TSPAN33.

Liver: ABCC2, ABCG5, ABCG8, AHSG, AKR1C4, AMDHD1, APOH, ASGR1, ASGR2, C3P1, C8A, C8B, C9, CASA, CFHR4, CPN2, CREB3L3, CYP2B6, CYP2C9, CYP2E1, CYP3A4, DHODH, F12, F2, F7, GC, HAL, HPD, HPX, INHBC, ITIH1, ITIH2, ITIH3, KNG1, LBP, PGLYRP2, PLG, PROC, PRODH2, SERPINA6, SERPINC1, SLC13A5, SLC22A1, SLC25A47, SLC27A5, SULT2A1, TFR2, TMPRSS6, and UROC1.

Lung: ANXA3, BMP5, CYP4Z2P, DRAM1, FMO2, GNA15, IDOL KCNS3, LIMCH1, MBIP, PAPSS2, PCDH17, RSPH4A, RTKN2, and TRPC6.

Lymph nodes: ACAP1, AKNA, ARHGAP9, BCL11B, BIRC3, CARD11, CD180, CD37, CD3E, CD3G, CD40, CETP, CIITA, CLEC2D, CNR2, CXCR5, DOCK10, ETS1, GPR132, GPR18, ICAM2, ICOS, ITGB7, ITK, KIAA1551, KLHL6, LCK, LINC00426, LY86, MDS2, MEOX2, MX2, NAPSB, PATL2, PCED1B-AS1, PIK3CD, PLVAP, POU2F2, SCIMP, SCML4, SLFN12L, SMAP2, SP110, SPIB, TLR10, TMC8, TMEM156, TNFAIP8, TNFRSF9, TNFSF11, TRAF1, TRIM22, UCP2, and ZC3H12D.

Ovary: ABCA10, ACSS3, ADAMTS5, AQP11, C7, CDH3, CDON, CLDN11, COL14A1, COLEC11, ESR2, FAM198B, FZD3, GALNT10, GLI2, GSTM5, HS3ST1, LEMD1-AS1, LHX9, LRRC17, MCHR1, MRC2, NTF3, OMD, PDGFRA, PGR, PKNOX2, PTCH2, RWDD4, SCD5, SERPINE2, SIMC1, SLC25A17, SNCAIP, SULF2, TENM4, TSPAN5, TTC8, and UBXN8.

Pancreas: ALDH1L2, ANKEF1, ASNS, B3GALNT2, BCAT1, CASP9, CCDC110, CELA2B, CELA3B, CFTR, CHMP4C, CLDN1, CNIH3, COCH, CUZD1, DEFB1, EGF, EIF4EBP1, ERP27, FAM24B-CUZD1, FBXW12, GUCA1C, KCTD16, KIAA1324, LINC00339, LNX2, MKNK1, NAA16, NPHS1, PAIP2B, PM20D1, PRSS3, SCGN, SEL1L, SERPINI2, SH3YL1, SLC33A1, SLC4A4, TC2N, TDH, TMEM51-AS1, TRHDE, and UMOD.

Placenta: ADAM12, ATG9B, ATP6V1C2, BCAR4, BMP1, BPGM, CSF3R, CYP11A1, CYP19A1, DACT2, DEPDC1B, DLX5, EBI3, GCM1, GPR78, GSTA3, IGF2BP3, IGSF5, ISM2, KISS1, KRT23, LIN28B, MMP11, PGF, PSG11, PSG2, PSG3, PSG6, PSG7, PSG8, SPTLC3, TPRXL, ZFAT, and ZNF554.

Prostate: ABCC4, ACPP, ALOX15B, ANO7, AP1B1P1, ARG2, BEND4, C6orf132, C6orf52, CANT1, CASZ1, CBFA2T2, CHRM1, CHRNA2, COL26A1, EVX1, EYA2, FAM135A, HMGN2P46, KLK2, KLKP1, MME, MPPED2, MUC12, NANS, NCAPD3, NEFH, NIPAL3, OACYLP, OR51E2, PAK1IP1, PDE9A, PI15, PMEPA1, POTEF, RDH11, SCNN1G, SIM2, SLC14A1, SLC22A3, SLC2A12, SLC30A4, SLC35F2, SLC37A1, SLC39A6, SPDEF, STEAP2, THSD4, TMEM79, TPM3P9, TXNDC16, URB1, VIPR1, ZNF350, ZNF532, ZNF613, ZNF649, ZNF761, and ZNF827.

Smooth muscle: GADL1, GIPC3, PTGES3L, and WSCD2.

Testis: CCDC27, DMRT1, DNAJC5G, FBXO24, IGLL1, MOV10L1, SEPT14, THEG, and TTC16.

(e) Differentially Represented Tissue-Specific Genes—Set 3:

The genes in Set 3 are organized as Sets 3A through 3S in Tables 1 through 19 according to tissue type, with each gene identified by name and chromosome location, with the relative contribution (determined using glmnet1A) identified. These genes are optimally useful for discriminating between tissue types using sets of hydroxymethylation profiles from multiple tissue input sources, while the genes of Sets 1 and 2 are exemplary for identifying an unknown tissue or cell sample using fitted models derived from hydroxymethylation profiles.

Set 3:

TABLE 1

Set 3A:
BLADDER

| ChromosomeName_GeneName | Relative Contribution |
|---|---|
| chr16_SNX29P1_ | 39.4 |
| chr10_CUTC_ | 38.9 |
| chr12_NT5DC3_ | 38.8 |
| chr17_RBFOX3_ | 29 |
| chr05_IL17B_ | 23.1 |
| chr12_GTSF1_ | 22.5 |
| chr01_FMO1_ | 20.1 |
| chr10_NEBL_ | 18.4 |
| chr07_CLEC2L_ | 18.2 |
| chr17_TBX4_ | 16.9 |
| chr10_TACR2_ | 14.9 |
| chr09_TMOD1_ | 13.6 |
| chr20_C20orf166_ | 13.2 |
| chr16_LOC732275_ | 12.9 |
| chr07_TPST1_ | 11.2 |

TABLE 1-continued

| Set 3A: BLADDER | |
|---|---|
| ChromosomeName__GeneName | Relative Contribution |
| chr17__P2RX1__ | 9.5 |
| chr01__HIST2H2BF__ | 7 |
| chr02__C2orf40__ | 2 |

TABLE 2

| Set 3B: BONE MARROW | |
|---|---|
| ChromosomeName__GeneName | Relative Contribution |
| chr10__KCNK18__ | 52.8 |
| chr12__LRP6__ | 34.1 |
| chr19__TARM1__ | 27.1 |
| chr12__NUAK1__ | 25.3 |
| chr15__TJP1__ | 24.6 |
| chr05__HK3__ | 24.5 |
| chr01__NDUFS5__ | 22.8 |
| chr19__CEACAM8__ | 21.6 |
| chr12__BCL2L14__ | 20.4 |
| chr02__AGAP1__ | 19.9 |
| chr06__SLC22A16__ | 18 |
| chr04__FAT1__ | 17.9 |
| chr05__PPAP2A__ | 17.5 |
| chr17__CRK__ | 13.5 |
| chr19__LYPD4__ | 11 |
| chr10__BMPR1A__ | 10.1 |
| chr14__APOPT1__ | 9.1 |
| chr01__S100A9__ | 6.9 |
| chr19__VSTM1__ | 6.4 |
| chr02__FAM168B__ | 6.3 |
| chr16__MEFV__ | 6.2 |
| chr10__VDAC2__ | 6.1 |
| chr13__FARP1__ | 5.7 |
| chr19__CEACAM4__ | 5.6 |
| chr06__SASH1__ | 5.5 |
| chr03__FLNB__ | 4.1 |
| chr16__ADCY9__ | 3.9 |
| chr03__WWTR1__ | 3.1 |
| chr02__LOC339803__ | 2.6 |
| chr12__SP1__ | 2.2 |
| chr12__LRIG3__ | 1.3 |
| chr13__RNF113B__ | 1 |
| chr17__LPO__ | 0.5 |
| chr15__CYFIP1__ | 0.3 |

TABLE 3

| Set 3C: BRAIN | |
|---|---|
| ChromosomeName__GeneName | Relative Contribution |
| chr10__ZNF503.AS2__ | 72.4 |
| chr05__LRRTM2__ | 63 |
| chr02__CCDC140__ | 43.8 |
| chr05__FLJ35946__ | 42 |
| chr01__DMRTA2__ | 39.3 |
| chr12__TUBA1A__ | 33.3 |
| chr01__HAPEN2__ | 20.8 |
| chr22__LOC150381__ | 17.4 |
| chr03__ZIC1__ | 17.2 |
| chr01__CAMK2N1__ | 16 |
| chr03__EIF4A2__ | 15.5 |
| chr10__VAX1__ | 13.3 |
| chr08__HEY1__ | 12.1 |
| chr11__HSPA8__ | 9.5 |
| chr03__EGOT__ | 7.7 |

TABLE 3-continued

| Set 3C: BRAIN | |
|---|---|
| ChromosomeName__GeneName | Relative Contribution |
| chr17__DDX5__ | 2.7 |
| chr17__TOB1__ | 0.8 |
| chr13__AMER2__ | 0.5 |

TABLE 4

| Set 3D: BREAST | |
|---|---|
| ChromosomeName__GeneName | Relative Contribution |
| chr12__KCNA1__ | 59.1 |
| chr02__NPPC__ | 54.5 |
| chr11__ALX4__ | 45.6 |
| chr11__GAL__ | 41 |
| chr19__SBK2__ | 32.1 |
| chr18__RBBP8__ | 26.1 |
| chr21__LINC00323__ | 23.1 |
| chr20__TSHZ2__ | 22.7 |
| chr09__LHX6__ | 22.6 |
| chr02__WNT6__ | 18.4 |
| chr01__LRRC71__ | 15.1 |
| chr11__LOC650368__ | 13.6 |
| chr17__PIK3R6__ | 12.4 |
| chr18__GRP__ | 10.4 |
| chr17__RNASEK__ | 9.7 |
| chr05__FOXI1__ | 7.5 |
| chr02__TBR1__ | 3.4 |
| chr01__LOC339505__ | 2.8 |
| chr08__LZTS1.AS1__ | 2.4 |

TABLE 5

| Set 3E: COLON (SIGMOID) | |
|---|---|
| ChromosomeName_GeneName | Relative Contribution |
| chr14_CBLN3_ | 57.3 |
| chr03_NRADDP_ | 53.1 |
| chr01_SERTAD4.AS1_ | 41.2 |
| chr01_ATPAF1_ | 41.2 |
| chr11_CALCB_ | 36.1 |
| chr16_ZNF764_ | 32.8 |
| chr20_SNRPB2_ | 29.7 |
| chr01_AMIGO1_ | 29.1 |
| chr07_MUC12_ | 25.1 |
| chr16_PDIA2_ | 22 |
| chr19_JOSD2_ | 21.6 |
| chr02_IGFBP2_ | 20.8 |
| chr19_HMG20B_ | 20 |
| chr22_CHADL_ | 16.2 |
| chr01_DUSP23_ | 13.5 |
| chr22_TUBA3FP_ | 12.5 |
| chr11_KLHL35_ | 12.4 |
| chr06_TOMM6_ | 11.5 |
| chr11_TRPT1_ | 9.9 |
| chr07_NSUN5P1_ | 8.2 |
| chr02_LOC375196_ | 8.1 |
| chr06_LOC729603_ | 7.4 |
| chr19_ANGPTL4_ | 6.7 |
| chr07_NSUN5_ | 4.2 |
| chr13_RBM26.AS1_ | 4 |
| chr08_GRINA_ | 3.7 |
| chr01_TSSK3_ | 3.4 |
| chr20_RBBP9_ | 1.8 |
| chr16_PRSS53_ | 0.3 |

TABLE 6

| Set 3F: COLON (TRANSVERSE) | |
|---|---|
| ChromosomeName_GeneName | Relative Contribution |
| chr09_DPM2_ | 63.7 |
| chr01_AURKAIP1_ | 60.4 |
| chr01_DCDC2B_ | 37.7 |
| chr01_TAGLN2_ | 33.5 |
| chr02_FAHD2B_ | 29.6 |
| chr11_CDKN1C_ | 29.4 |
| chr22_TNFRSF13C_ | 27.8 |
| chr02_C2orf27B_ | 25 |
| chr08_SLURP1_ | 22.5 |
| chr11_TAGLN_ | 20.6 |
| chr17_B4GALNT2_ | 19 |
| chr07_RASA4CP_ | 15.9 |
| chr06_SPACA1_ | 13.3 |
| chr19_PAFAH1B3_ | 12 |
| chr11_LOC100652768_ | 11.9 |
| chr07_CYCS_ | 11.4 |
| chr17_TLCD1_ | 9.5 |
| chr17_XYLT2_ | 9.5 |
| chr20_PCK1_ | 8.8 |
| chr02_FABP1_ | 6.7 |
| chr17_ACADVL_ | 6.4 |
| chr17_NPTX1_ | 6.2 |
| chr05_TRIM7_ | 5.5 |
| chr16_RPS2_ | 5.4 |
| chr13_NEK3_ | 5.1 |
| chr01_LEFTY1_ | 4.6 |
| chr01_S100A4_ | 4 |
| chr03_C3orf45_ | 2.8 |
| chr16_TBC1D10B_ | 2.3 |
| Chr17_GP1BA_ | 1.4 |

TABLE 7

| Set 3G: GASTROINTESTINAL | |
|---|---|
| ChromosomeName_GeneName | Relative Contribution |
| chr03_CLDN18_ | 87.7 |
| chr02_GKN1_ | 64 |
| chr01_CAPN8_ | 46.4 |
| chr21_TFF1_ | 42.2 |
| chr01_FAM177B_ | 41.2 |
| chr02_GKN2_ | 38.7 |
| chr04_ANXA10_ | 38.1 |
| chr02_SULT1C2_ | 37.7 |
| chr08_FER1L6_ | 15.2 |
| chr03_NAALADL2.AS3_ | 0.4 |

TABLE 8

| Set 3H: HEART | |
|---|---|
| ChromosomeName_GeneName | Relative Contribution |
| chr02_TTN.AS1_ | 49.5 |
| chr05_PCDHGA5_ | 48.7 |
| chr05_PCDHGB3_ | 41.7 |
| chr05_PCDHGA6_ | 37.3 |
| chr05_PCDHGA7_ | 26.3 |
| chr05_MIR548AO_ | 22.9 |
| chr05_PCDHGB4_ | 19.5 |
| chr03_SCN5A_ | 17.5 |
| chr19_TNNT1_ | 15 |
| chr02_ASB18_ | 13.5 |
| chr05_PCDHGA8_ | 13 |
| chr19_ZNF256_ | 9.4 |

TABLE 8-continued

| Set 3H: HEART | |
|---|---|
| ChromosomeName_GeneName | Relative Contribution |
| chr03_FGF12_ | 6.6 |
| chr03_FBXO40_ | 4.7 |
| chr05_PCDHGB5_ | 4 |

TABLE 9

| Set 3I: HYPOTHALAMUS | |
|---|---|
| ChromosomeName_GeneName | Relative Contribution |
| chr12_BHLHE41_ | 53.6 |
| chr11_COX8A_ | 48 |
| chr02_GBX2_ | 47.4 |
| chr11_FAM181B_ | 31.4 |
| chr10_LINC00200_ | 24.4 |
| chr11_ZNHIT2_ | 22.5 |
| chr01_FAM43B_ | 21.3 |
| chr15_APBA2_ | 21.2 |
| chr21_KCNJ15_ | 19.3 |
| chr10_C10orf114_ | 17.1 |
| chr05_NPR3_ | 16.6 |
| chr07_DPP6_ | 14 |
| chr08_ADRB3_ | 13.5 |
| chr18_CDH20_ | 13.5 |
| chr07_ZNF479_ | 11.2 |
| chr09_SSNA1_ | 7.4 |
| chr12_GAPDH_ | 7.2 |
| chr06_QKI_ | 5.3 |
| chr11_NTM_ | 4.5 |
| chr10_ADARB2_ | 4.3 |
| chr04_HMX1_ | 3.5 |
| chr03_LINC00606_ | 3.3 |
| chr11_KIRREL3.AS2_ | 2.4 |
| chr05_C5orf64_ | 2.4 |
| chr08_NKX2.6_ | 2 |
| chr11_ASCL2_ | 0.8 |
| chr19_ETV2_ | 0.7 |
| chr18_SALL3_ | 0.6 |
| chr03_ZDHHC23_ | 0.5 |

TABLE 10

| Set 3J: KIDNEY | |
|---|---|
| ChromosomeName_GeneName | Relative Contribution |
| chr10_PAX2_ | 82.5 |
| chr02_GALNT14_ | 47.8 |
| chr12_CCDC64_ | 44 |
| chr02_LOC654433_ | 34.2 |
| chr15_PAQR5_ | 34.1 |
| chr01_DNAJC11_ | 21.3 |
| chr12_LOC100130238_ | 15.9 |
| chr02_EMX1_ | 12.6 |
| chr13_C13orf35_ | 9.3 |
| chr16_CDH16_ | 6.6 |
| chr19_FUT3_ | 5.4 |
| chr22_BCRP3_ | 4.5 |
| chr02_PAX8_ | 4.5 |
| chr01_SEMA4A_ | 3.4 |
| chr15_IL16_ | 0.8 |
| chr10_OGDHL_ | 0.7 |
| chr17_LOC284100_ | 0.2 |

TABLE 11

Set 3K: LIVER

| ChromosomeName_GeneName | Relative Contribution |
|---|---|
| chr02_APOB_ | 61.3 |
| chr10_CYP2E1_ | 34 |
| chr03_ITIH1_ | 32.8 |
| chr05_F12_ | 30.5 |
| chr10_ITIH2_ | 26.1 |
| chr02_ABCG8_ | 23.7 |
| chr11_F2_ | 23 |
| chr03_ITIH4_ | 17.2 |
| chr03_NR1I2_ | 15 |
| chr17_ASGR2_ | 12.9 |
| chr10_GPAM_ | 10.8 |
| chr15_AQP9_ | 8.8 |
| chr06_PLG_ | 7.9 |
| chr17_SLC13A5_ | 2.7 |
| chr12_AMDHD1_ | 0.6 |
| chr20_LBP_ | 0.1 |

TABLE 12

Set 3L: LUNG

| ChromosomeName_GeneName | Relative Contribution |
|---|---|
| chr03_CCR5_ | 89 |
| chr06_GPR116_ | 49.7 |
| chr01_TDRD10_ | 45.9 |
| chr01_SHE_ | 43.5 |
| chr10_MYOZ1_ | 28.8 |
| chr15_FAM108C1_ | 28.4 |
| chr19_ICAM5_ | 21.8 |
| chr06_MLLT4.AS1_ | 20 |
| chr05_GDNF_ | 20 |
| chr04_KDR_ | 14.3 |
| chr12_ALDH2_ | 13.5 |
| chr19_KANK3_ | 12.5 |
| chr12_RILPL2_ | 10.1 |
| chr01_TACSTD2_ | 8.8 |
| chr20_GGTLC1_ | 4.9 |
| chr19_ICAM1_ | 0.3 |

TABLE 13

Set 3M: LYMPH NODE

| ChromosomeName_GeneName | Relative Contribution |
|---|---|
| chr19_SPIB_ | 54.5 |
| chr12_HVCN1_ | 48.2 |
| chr01_PIK3CD_ | 42.9 |
| chr08_BLK_ | 21.5 |
| chr11_GSTP1_ | 20.4 |
| chr19_FCER2_ | 19.2 |
| chr17_SCIMP_ | 19.2 |
| chr15_LOC388152_ | 18.7 |
| chr19_BST2_ | 17 |
| chr07_CARD11_ | 14.3 |
| chr19_CD37_ | 13.8 |
| chr19_NOSIP_ | 12 |
| chr07_ATP6V0E2.AS1_ | 11.6 |
| chr09_TRAF1_ | 11 |
| chr01_IL10_ | 10.5 |
| chr01_ARHGAP30_ | 10.4 |
| chr16_IL21R.AS1_ | 9.4 |
| chr02_DAPL1_ | 9.4 |
| chr17_ICAM2_ | 5.7 |
| chr05_ITK_ | 5.7 |
| chr08_TNFRSF10A_ | 5.2 |
| chr01_RHD_ | 4.9 |

TABLE 13-continued

Set 3M: LYMPH NODE

| ChromosomeName_GeneName | Relative Contribution |
|---|---|
| chr01_SMAP2_ | 4.5 |
| chr06_TAP1_ | 3.4 |
| chr16_CD19_ | 3.2 |
| chr20_MYBL2_ | 0.8 |

TABLE 14

Set 3N: OVARY

| ChromosomeName_GeneName | Relative Contribution |
|---|---|
| chr01_KLHDC8A_ | 61.8 |
| chr02_TCF23_ | 52.2 |
| chr11_WT1_ | 43.2 |
| chr11_AQP11_ | 36.9 |
| chr01_LHX9_ | 32.9 |
| chr07_TSGA13_ | 31.9 |
| chr12_BTBD11_ | 16.3 |
| chr16_CDH3_ | 13.6 |
| chr02_GREB1_ | 11.9 |
| chr17_ATP1B2_ | 10.7 |
| chr01_LEMD1.AS1_ | 7.6 |
| chr05_LOC643201_ | 7.6 |
| chr19_NXNL1_ | 2.2 |

TABLE 15

Set 3O: PANCREAS

| ChromosomeName_GeneName | Relative Contribution |
|---|---|
| chr08_EIF4EBP1_ | 63 |
| chr10_SFRP5_ | 31.8 |
| chr01_TMEM51.AS1_ | 30.1 |
| chr19_NPHS1_ | 28 |
| chr16_UMOD_ | 27.8 |
| chr01_NR5A2_ | 26.6 |
| chr01_KIAA1324_ | 22.5 |
| chr01_ERO1EB_ | 21 |
| chr13_DZIP1_ | 20.7 |
| chr15_HOMER2_ | 15.2 |
| chr04_TMEDHP_ | 13.9 |
| chr13_CLDN10_ | 11.9 |
| chr06_LINC00222_ | 11.4 |
| chr20_RBPJL_ | 6.6 |
| chr06_SLC16A10_ | 5.9 |
| chr08_TDH_ | 0.8 |

TABLE 16

Set 3P: PLACENTA

| Gene | Relative Contribution |
|---|---|
| chr19_DPRX_ | 45.6 |
| chr08_CYP7B1_ | 30.6 |
| chr01_HSD3B1_ | 29 |
| chr02_ZFP36L2_ | 22 |
| chr07_IGF2BP3_ | 22 |
| chr18_MBP_ | 20.7 |
| chr13_METTL21C_ | 19 |
| chr01_AIM1L_ | 17.4 |
| chr13_WASF3_ | 17.4 |
| chr02_RGPD1_ | 16.9 |
| chr15_CYP19A1_ | 16.3 |

TABLE 16-continued

| Set 3P: PLACENTA | |
|---|---|
| Gene | Relative Contribution |
| chr02_RGPD2_ | 16 |
| chr01_ADCY10_ | 12.6 |
| chr15_SLCO3A1_ | 9.6 |
| chr07_SLC13A4_ | 7.2 |
| chr16_C16orf45_ | 6.3 |
| chr06_LIN28B_ | 5.2 |
| chr17_RNF222_ | 4.7 |
| chr04_TENM3_ | 4.6 |
| chr15_SH2D7_ | 2.7 |
| chr19_LGALS14_ | 1.9 |
| chr19_CLEC4GP1_ | 1.8 |
| chr16_SPIRE2_ | 1.5 |
| chr08_C8orf42_ | 0.4 |
| chr05_LOC728613_ | 0.1 |

TABLE 17

| Set 3Q: PROSTATE | |
|---|---|
| ChromosomeName_GeneName | Relative Contribution |
| chr22_NEFH_ | 71.2 |
| chr19_KLKP1_ | 53.9 |
| chr06_SPDEF_ | 50.4 |
| chr03_ACPP_ | 42.5 |
| chr18_SLC14A1_ | 32.8 |
| chr19_ZNF350_ | 20.2 |
| chr07_HOXA13_ | 18.5 |
| chr15_SLC30A4_ | 15.2 |
| chr17_KRT14_ | 12.5 |
| chr15_USP50_ | 10.8 |
| chr06_C6orf52_ | 10.1 |
| chr18_OACYLP_ | 8.5 |
| chr19_KLK2_ | 8.4 |
| chr20_EYA2_ | 3.8 |
| chr10_LOC283038_ | 3.1 |
| chr15_LMAN1L_ | 2.3 |
| chr02_HOXD10_ | 2.2 |
| chr02_PPP1R7_ | 1.8 |

TABLE 18

| Set 3R: SKIN | |
|---|---|
| ChromosomeName_GeneName | Relative Contribution |
| chr14_C14orf177_ | 100 |
| chr19_SBSN_ | 83.2 |
| chr06_C6orf132_ | 35 |
| chr08_LOC340357_ | 31.4 |
| chr18_CD226_ | 23.7 |
| chr05_AHRR_ | 22.4 |
| chr07_HOXA11.AS_ | 19.2 |
| chr14_BCL11B_ | 18.6 |
| chr06_RAB44_ | 14.6 |
| chr10_FAM25A_ | 12.3 |
| chr05_IRX1_ | 8.5 |
| chr02_SLC35F6_ | 7.9 |
| chr18_RAX_ | 6.8 |
| chr07_MIR548T_ | 6.8 |
| chr12_KRT1_ | 6.7 |
| chr16_HS3ST6_ | 5.4 |
| chr02_PTPN4_ | 4.3 |
| chr07_GPNMB_ | 4.2 |
| Chr17_FAM57A_ | 1.4 |

TABLE 19

| Set 3S: TESTIS | |
|---|---|
| Gene | Relative Contribution |
| chr05_FAM153C_ | 62.9 |
| chr20_DEFB123_ | 44.9 |
| chr16_LITAF_ | 40.3 |
| chr18_ZADH2_ | 36.1 |
| chr09_DMRT1_ | 34.4 |
| chr01_EPS8L3_ | 26.3 |
| chr01_CCDC27_ | 26.3 |
| chr04_SMAD1_ | 24.5 |
| chr11_C11orf91_ | 22.2 |
| chr07_C1GALT1_ | 22.1 |
| chr03_NFKBIZ_ | 17.1 |
| chr20_RIMS4_ | 12.6 |
| chr07_PRSS1_ | 12.4 |
| chr09_OBP2B_ | 10.9 |
| chr12_KRT6A_ | 9.4 |
| chr12_CDK17_ | 8.9 |
| chr21_TEKT4P2_ | 8.7 |
| chr05_ANKRD33B_ | 8.4 |
| chr14_RNASE1_ | 8.2 |
| chr12_PTMS_ | 8.2 |
| chr03_LRRC2_ | 4 |
| chr02_SLC30A3_ | 2.7 |
| chr14_IFI27L1_ | 1.4 |
| chr07_C7orf33_ | 0.1 |

(f) Comparison of Sample Hydroxymethylation Profile with Reference Profiles:

The tissue assignment method next involves comparing the hydroxymethylation profile detected in (a) with the reference profiles in the reference data set. For ease of comparison, the detected hydroxymethylation profile should be generated in a form that is the same as that of the reference hydroxymethylation profiles, with regard to the type, amount, and format of data in the profile.

The comparison between the hydroxymethylation profile of the sample DNA and the hydroxymethylation profiles in the reference data set involves an analysis of the sample hydroxymethylation profile across the plurality of hydroxymethylation vectors in the data set. Individual data points may be, for example, the presence or absence of hydroxymethylation at a particular site in both the sample and one or more reference hydroxymethylation profiles; a higher or lower hydroxymethylation density at a particular locus in the sample relative to one or more reference hydroxymethylation profiles; and the like.

The comparison of sample hydroxymethylation profile across a large number of reference hydroxymethylation profiles in the reference data set can be carried out using art-recognized methods of assessing similarity across a plurality of features, and any appropriate state of the art mathematical method can be used. Well-known mathematical methods for establishing correlation between data sets employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods, as explained earlier herein. Selection of use of an appropriate mathematical method to evaluate a detected hydroxymethylation profile in a comparison across a large reference set of reference hydroxymethylation vectors is within the skill of the art and, as such, is not described in detail.

Details relating to these statistical methods are found in the following references: Ruczinski et al. (2003) *J. Computational and Graphical Statistics* 12:475-511 (2003); Friedman (1989) *J. Amer. Statistical Assoc.* 84:165-175; Hastie et al., *The Elements of Statistical Learning*, Springer Series in Statistics (2001); Breiman et al., *Classification and Regression Trees* (Wadsworth Publishing, 1984); Breiman (2001) *Machine Learning* 45:5-32; Pepe, *The Statistical Evaluation of Medical Tests for Classification and Prediction*, Oxford Statistical Science Series, 28 (2003); and Duda et al., *Pattern Classification* (Wiley Interscience, 2nd Edition, 2001). In some techniques, it is desirable to generate a hydroxymethylation difference data set that comprises differences identified between the hydroxymethylation profile of the DNA sample and each of the plurality of reference hydroxymethylation profiles.

The similarities and differences between the hydroxymethylation profile of a DNA sample and the set of reference hydroxymethylation profiles are thus analyzed and, based on the analysis, a tissue of origin is probabilistically assigned to the sample DNA. The result may be a probability in the form of a percentage likelihood that the tissue of origin is a specific tissue, e.g., bone marrow tissue, lung tissue, or the like. The result may also be in the form of two or more probabilities each in the form of a percentage likelihood that the tissue of origin is from the different tissues. The latter result might take the form of a list of tissues with corresponding probabilities, e.g., the result for one DNA sample might read as follows: breast tissue, 79%; uterine tissue, 11%; endometrial tissue, 10%. Other methods for presenting the result or results obtained can also be envisioned and adapted by one of ordinary skill in the art for a particular purpose.

Providing that the hydroxymethylation profiles in the reference data set are sufficiently tissue-specific, and/or that the combination of hydroxymethylation profiles gives rise to a statistically significant result following comparison with the sample DNA hydroxymethylation profile, the method of the invention characterizes the tissue of origin with both high sensitivity and high specificity.

3. Related Methods of Use

The hydroxymethylation vectors within the reference set may include "normal" hydroxymethylation profiles, i.e., hydroxymethylation profiles for reference loci associated with tissue-specific genes in subjects who do not exhibit any pathology vis-à-vis the particular tissue or organ with which a particular reference locus is associated. The hydroxymethylation vectors may also include hydroxymethylation profiles that are associated with:

- an adverse condition, disorder, or disease of a particular tissue, such as the presence of a tumor, neoplasm, or cancer;
- the likelihood of developing an adverse condition, disorder, or disease of a particular tissue, such as a tumor, neoplasm or cancer (in which case the method may be implemented to detect a premalignant condition);
- the likelihood that a subject who is adversely affected by a particular condition, disease or disorder will be a responder to a particular course of treatment; and/or
- the likelihood that a subject who is adversely affected by a particular condition, disease or disorder is responding to a particular course of treatment.

Accordingly, in a further embodiment of the invention, a method is provided for detecting the condition of a tissue or organ in a human subject, which involves: (a) generating a hydroxymethylation profile of DNA in a cell-free fluid sample obtained from the subject; (b) comparing the hydroxymethylation profile generated in (a) with each of a plurality of reference hydroxymethylation profiles in a reference set, each reference hydroxymethylation profile associated with (i) a reference locus associated with a tissue-specific gene and (ii) a condition of a specific tissue or organ; and (c) based on a comparison of the hydroxymethylation profile generated for the subject with the reference hydroxymethylation profiles, identifying the condition of the specific tissue or organ in the subject.

The method may additionally include making a diagnosis, a treatment decision, or a prognosis based on the identified condition of the specific tissue or organ in the subject.

In a related embodiment, the invention provides a method for detecting a change in the condition of a tissue or organ in a human subject, comprising: (a) generating an initial hydroxymethylation profile at one or more loci of DNA fragments in a cell-free fluid sample obtained from the subject, where the hydroxymethylation profile is associated with an initial condition of a tissue or organ; (b) at a later time, generating a subsequent hydroxymethylation profile at the same one or more loci in a cell-free fluid sample obtained from the subject; and (c) comparing the subsequent hydroxymethylation profile with the initial hydroxymethylation profile to detect a change in the condition of a tissue or organ.

The aforementioned method may involve repetition of step (b) at one or more additional times so as to monitor the progress of a condition, disease or disorder associated with the tissue or organ, i.e., in the context of an ongoing patient evaluation. The method enables ready assessment of the efficacy of a therapeutic intervention, e.g., ongoing pharmacotherapy or the like, with respect to the condition, disease or disorder of the affected tissue or organ. The method may also involve monitoring changes in gene expression over time, i.e., throughout the patient evaluation period.

In another related embodiment, the invention provides a method for determining the likelihood that a subject will develop an adverse condition, disease, or disorder of a particular tissue or organ, where the method involves: (a) generating a hydroxymethylation profile at one or more loci of DNA fragments in a cell-free fluid sample obtained from the subject, where the hydroxymethylation profile is associated with a likelihood of developing an adverse condition, disease, or disorder of a particular tissue or organ; (b) comparing the hydroxymethylation profile generated in (a) with each of a plurality of reference hydroxymethylation profiles in a reference set, each reference hydroxymethylation profile associated with (i) a reference locus associated with a tissue-specific gene and (ii) a likelihood of developing an adverse condition, disease, or disorder of a specific tissue or organ; and (c) based on a comparison of the hydroxymethylation profile generated for the subject with the reference hydroxymethylation profiles, identifying the likelihood that the subject will develop an adverse condition, disease, or disorder of the specific tissue or organ.

Applications of particular interest include the characterization of a cancer of a particular tissue as a carcinoma, sarcoma, lymphoma, leukemia, germ cell tumor, blastoma, or the like, as described in detail in U.S. Patent Publication No. US 2017/0298422 to Song et al., previously incorporated by reference herein.

Carcinomas include, without limitation, epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, Hurthle cell adenoma, renal cell carcinoma, Grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, Warthin's tumor, thymoma, specialized gonadal neoplasms, sex cord stromal tumor, thecoma, granulosa cell tumor, arrhenoblastoma, Sertoli-Leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes, without limitation, Askin's tumor, botryoides, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma. Lymphoma and leukemia include, without limitation, chronic lymphocytic leukemia/small lymphocytic lymphoma, B-cell prolymphocytic leukemia, lymphoplasmacytic lymphoma (such as Waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, Burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides, Sézary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical Hodgkin lymphomas (nodular sclerosis, mixed cellularity, lymphocyte-rich, lymphocyte depleted or not depleted), and nodular lymphocyte-predominant Hodgkin lymphoma. Germ cell tumors include without limitation germinoma, dysgerminoma, seminoma, nongerminomatous germ cell tumor, embryonal carcinoma, endodermal sinus tumor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non-small cell lung cancer and small cell lung cancer (including small cell carcinoma (oat cell cancer), mixed small cell/large cell carcinoma, and combined small cell carcinoma), colon cancer, breast cancer, prostate cancer, liver cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

The cancer may be an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor. The methods of the invention can be used to assign a likelihood that a subject's hydroxymethylation profile is indicative of one or more of the foregoing cancers.

One aspect of this embodiment pertains to Carcinomas of Unknown Primary (CUP), a disease in which malignant cells are found within the body, i.e., metastasis has occurred, but the tissue of origin of the primary cancer is unknown. The methods of the invention are useful in this context, insofar as a tissue of origin can be probabilistically assigned to CUPs.

Comparison of the hydroxymethylation profile of sample DNA with the tissue-specific hydroxymethylation profiles in the reference data set can also provide information about cardiovascular disease, such as atherosclerosis, congestive heart failure, vulnerable plaque, stroke, or ischemia. The cardiovascular disease or condition can be high blood pressure, stenosis, vessel occlusion or a thrombotic event. Other information by provided by the comparison relates to organ toxicology. As one example, the presence of UR genes in the liver or kidney might indicate the toxicity of a particular pharmacologically active agent. As another example, UR genes are useful in ascertaining the extent of cell death within an organ. As an additional example, a combination of UR and DE genes is useful in identifying cell dysfunction within an organ.

Other adverse conditions, disorders, and diseases that are tissue-specific are also of interest herein, and include, without limitation, inflammatory diseases, immune diseases, autoimmune diseases, neurological diseases, and infectious diseases, described in U.S. Patent Publication No. US 2017/0298422 to Song et al.

In a further embodiment, any of the above-described methods can be combined with a methylation analysis. Methods for the determination of methylation profiles are known. This embodiment involves the determination of a sample DNA methylation profile and its use in an expanded comparison, wherein in addition to the hydroxymethylation analysis, methylation profiles are compared as well, using a reference set of methylation profiles analogous to the hydroxymethylation profile reference set. A preferred method involves the generation of a DNA methylation profile and a hydroxymethylation profile from a single DNA sample, as described in Provisional U.S. Patent application Ser. No. 62/630,798 to Arensdorf and U.S. Patent Publication No. 2017/0298422 to Song et al., incorporated by reference earlier herein.

In another embodiment, an improved method is provided for analyzing a cell-free DNA sample obtained from human plasma in which cell-free DNA fragments in the sample are isolated, amplified, and sequenced, wherein the improvement comprises identifying contamination of the sample with genomic material originating from peripheral blood mononuclear cells (PBMCs) by: (a) generating a hydroxymethylation profile of DNA fragments in the cell-free sample; and (b) comparing the hydroxymethylation profile generated in (a) with each of a plurality of reference hydroxymethylation profiles in a reference set, each reference hydroxymethylation profile associated with a reference locus corresponding to a tissue-specific gene, wherein the reference hydroxymethylation profiles include at least one PBMC hydroxymethylation profile; and (c) identifying, from the comparison, the presence of genomic material originating from PBMCs. The method can also include estimating the level of PBMC genomic contamination from (b) and (c), and making a determination as to whether the sample is suitable for cell-free DNA analysis based on the level of PBMC genomic contamination. In this embodiment, the reference set optionally comprises a vector of a plurality of reference hydroxymethylation profiles each corresponding to a gene locus associated with a PBMC sub-type, i.e., lymphocytes including T cells, B cells, and NK cells; monocytes; and dendritic cells.

The invention claimed is:

1. A method for probabilistically assigning a tissue of origin to cell-free DNA (cfDNA) in a fluid sample obtained from a human subject, comprising:

(a) analyzing the cfDNA in the fluid sample by assessing hydroxymethylation levels within the cfDNA at each of a plurality of hydroxymethylation biomarker loci to generate a sample hydroxymethylation profile, wherein each biomarker locus is contained within a differentially hydroxymethylated genomic region associated with a tissue-specific gene that is both differentially represented and differentially expressed with respect to tissue of origin, and further wherein the biomarker loci analyzed represent at least 5 tissue types and at least 5 genes per tissue;

(b) comparing each assessed hydroxymethylation level in the sample hydroxymethylation profile with a corresponding reference hydroxymethylation level at each biomarker locus analyzed, the reference hydroxymethylation levels being contained within a plurality of different tissue-specific reference hydroxymethylation profiles in a reference data set, thereby generating a hydroxymethylation difference data set comprising differences identified between the generated sample hydroxymethylation profile and the reference hydroxymethylation profiles at each biomarker locus;

(c) using a computer system, carrying out a correlation analysis using one or more algorithms that determine a statistical correlation between the assessed hydroxymethylation levels and the reference hydroxymethylation levels at each biomarker locus; and (d) using the statistical correlation, providing a probabilistic assignment of at least one tissue of origin to the cfDNA.

2. The method of claim 1, wherein at least one of the hydroxymethylation biomarker loci is contained within a gene body or a component thereof.

3. The method of claim 2, wherein at least one hydroxymethylation biomarker locus is contained within an intron or exon.

4. The method of claim 1, wherein at least one of the hydroxymethylation biomarker loci is contained within a genomic annotation feature outside of the gene body.

5. The method of claim 4, wherein at least one hydroxymethylation biomarker locus is contained within a promoter, an enhancer, a transcription initiation site, a transcription stop site, a DNA binding site, or a combination thereof.

6. The method of claim 5, wherein at least one hydroxymethylation biomarker locus is contained within a DNA binding site comprising a silenced region or a transcription repressor binding site.

7. The method of claim 1, wherein the cfDNA comprises a plurality of cfDNA fragments, and the method further includes determining at least one of cfDNA length and cfDNA fragment distribution.

8. The method of claim 1, wherein the plurality of reference hydroxymethylation profiles in the reference data set comprise a hydroxymethylation profile of reference loci associated with at least five genes originating from each of five human tissue types comprising: adipose; adrenal gland; bladder; bone marrow; brain; breast; colon; cerebral cortex; cervical; uterine; digestive; endometrial; epididymal; esophageal; Fallopian tube; gall bladder; gastrointestinal; heart muscle; hypothalamus; kidney; liver; lung; lymph nodes; ovary; pancreas; parathyroid gland; placenta; prostate; salivary; seminal vesicle; skeletal muscle; smooth muscle; skin; spleen; stomach; testis; thyroid gland; or tonsil.

9. The method of claim 8, wherein the plurality of reference hydroxymethylation profiles in the reference data set comprise a hydroxymethylation profile of reference loci associated with at least five genes originating from each of five human tissue types comprising: bladder; bone marrow; brain; breast; colon; gastrointestinal; heart muscle; hypothalamus; kidney; liver; lung; lymph nodes; ovary; pancreas; placenta; prostate; skin; smooth muscle; or testis.

10. The method of claim 1, wherein each hydroxymethylation biomarker locus is contained within a differentially represented, differentially expressed gene comprising AARD, ADARB1, AKR1B10, CRYM-AS1, EPHA3, GTSF1, KCNMB1, MAP1B, NT5DC3, P2RX1, PCP4, PGM5, PLCD4, PTGFR, RBFOX3, SCARA3, SLIT3, SNX29P1, ST8SIA1, TBX4, TXNRD1, VCL, WFDC3, ABCA13, AZU1, CA1, CEACAM8, CLEC6A, DAZL, DRGX, DYTN, ELANE, FCAR, GFI1, GYPA, HK3, IL18RAP, LINC00333, LINC00550, LINC00558, LIPN, LOC100129620, LOC442028, LPO, MEFV, MMP8, MMP9, MPO, MS4A3, MYB, MYO1F, NCOR1P1, NME8, OR8U8, OSCAR, PARPBP, PAX3, PDCL2, PRDM13, PROK2, RGS18, RGS21, RRM2, RXFP2, SERPINB10, SLC22A16, SPATA16, SPI1, SPTA1, TARM1, TMPRSS15, TRIM58, VSTM1, XKR3, ASPHD1, BRSK1, CCDC177, CNTN2, HAPLN2, KCNJ10, KIF1A, LGI3, NCAN, NR2E1, RHBDL3, TMEM151A, TMEM235, TMEM59L, ZNF488, FGL2, SCNN1B, ADPRHL1, ASB18, ATP1A3, CDH13, CORO6, FSD2, GALNT16, GJA3, MYOM2, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB5, PCDHGB6, PCDHGB7, PXDNL, RPL3L, SGCG, TNNT1, ASTN1, DGK1, BBOX1, BCRP3, CA12, COL4A3, CXCL14, CYS1, EVC, FIGNL2, GALNT14, GLIS2, HAVCR1, LOC100130238, PAQR5, PAX2, PAX8, PLA2G15, SLC22A2, SLC9A3, SULT1C2, TSPAN33, ABCC2, ABCG5, ABCG8, AHSG, AKR1C4, AMDHD1, APOH, ASGR1, ASGR2, C3P1, C8A, C8B, C9, CASA, CFHR4, CPN2, CREB3L3, CYP2B6, CYP2C9, CYP2E1, CYP3A4, DHODH, F12, F2, F7, GC, HAL, HPD, HPX, INHBC, ITIH1, ITIH2, ITIH3, KNG1, LBP, PGLYRP2, PLG, PROC, PRODH2, SERPINA6, SERPINC1, SLC13A5, SLC22A1, SLC25A47, SLC27A5, SULT2A1, TFR2, TMPRSS6, UROC1, ANXA3, BMP5, CYP4Z2P, DRAM1, FMO2, GNA15, IDO1, KCNS3, LIMCH1, MBIP, PAPSS2, PCDH17, RSPH4A, RTKN2, TRPC6, ACAP1, AKNA, ARHGAP9, BCL11B, BIRC3, CARD11, CD180, CD37, CD3E, CD3G, CD40, CETP, CITA, CLEC2D, CNR2, CXCR5, DOCK10, ETS1, GPR132, GPR18, ICAM2, ICOS, ITGB7, ITK, KIAA1551, KLHL6, LCK, LINC00426, LY86, MDS2, MEOX2, MX2, NAPSB, PATL2, PCED1B-AS1, PIK3CD, PLVAP, POU2F2, SCIMP, SCML4, SLFN12L, SMAP2, SP110, SPIB, TLR10, TMC8, TMEM156, TNFAIP8, TNFRSF9, TNFSF11, TRAF1, TRIM22, UCP2, ZC3H12D, ABCA10, ACSS3, ADAMTS5, AQP11, C7, CDH3, CDON, CLDN11, COL14A1, COLEC11, ESR2, FAM198B, FZD3, GALNT10, GLI2, GSTM5, HS3ST1, LEMD1-AS1, LHX9, LRRC17, MCHR1, MRC2, NTF3, OMD, PDGFRA, PGR, PKNOX2, PTCH2, RWDD4, SCD5, SERPINE2, SIMC1, SLC25A17, SNCAIP, SULF2, TENM4, TSPAN5, TTC8, UBXN8, ALDH1L2, ANKEF1, ASNS, B3GALNT2, BCAT1, CASP9, CCDC110, CELA2B, CELABB, CFTR, CHMP4C, CLDN1, CNIH3, COCH, CUZD1, DEFB1, EGF, EIF4EBP1, ERP27, FAM24B-CUZD1, FBXW12, GUCA1C, KCTD16, KIAA1324, LINC00339, LNX2, MKNK1, NAA16, NPHS1, PAIP2B, PM20D1, PRSS3, SCGN, SEL1L, SERPINI2, SH3YL1, SLC33A1, SLC4A4, TC2N, TDH, TMEM51-AS1, TRHDE, UMOD, ADAM12, ATG9B, ATP6V1C2, BCAR4, BMP1, BPGM, CSF3R, CYP11A1, CYP19A1, DACT2, DEPDC1B, DLX5, EBI3, GCM1, GPR78, GSTA3, IGF2BP3, IGSF5, ISM2, KISS1, KRT23, LIN28B, MMP11, PGF, PSG11, PSG2, PSG3, PSG6, PSG7, PSG8, SPTLC3, TPRXL, ZFAT, ZNF554, ABCC4, ACPP, ALOX15B, ANO7, AP1B1P1, ARG2, BEND4, C6orf132, C6orf52, CANT1, CASZ1, CBFA2T2, CHRM1, CHRNA2, COL26A1, EVX1, EYA2, FAM135A, HMGN2P46, KLK2, KLKP1, MME, MPPED2, MUC12, NANS, NCAPD3, NEFH, NIPAL3, OACYLP, OR51E2, PAK1IP1, PDE9A, PI15, PMEPA1, POTEF, RDH11, SCNN1G, SIM2, SLC14A1, SLC22A3, SLC2A12, SLC30A4, SLC35F2, SLC37A1, SLC39A6, SPDEF, STEAP2, THSD4, TMEM79, TPM3P9, TXNDC16, URB1, VIPR1, ZNF350, ZNF532, ZNF613, ZNF649, ZNF761, ZNF827, GADL1, GIPC3, PTGES3L, WSCD2, CCDC27, DMRT1, DNAJC5G, FBXO24, IGLL1, MOV10L1, SEPT14, THEG, or TTC16.

11. The method of claim 1, wherein the reference hydroxymethylation profile comprises at least one of:

hydroxymethylation density within each hydroxymethylation biomarker locus;

total 5-hydroxymethylcytosine residues within each hydroxymethylation biomarker locus;

location of the 5-hydroxymethylcytosine residues within each hydroxymethylation biomarker locus;

identification of a hydroxymethylation biomarker locus as hemi-hydroxymethylated or fully hydroxymethylated; and relative positions of 5-hydroxymethylcytosine residues within each hydroxymethylation biomarker locus.

12. The method of claim 1, wherein the one or more algorithms comprises a tree-based method.

13. The method of claim 12, wherein the tree-based method comprises a regression model.

14. The method of claim 1, wherein the tissue-specific gene is a tissue-enriched gene.

15. The method of claim 1, wherein the reference data set comprises five or more data sets selected from the following:

| Set 3A: ChromosomeName_GeneName |
|---|
| chr16_SNX29P1_ |
| chr10_CUTC_ |
| chr12_NT5DC3_ |
| chr17_RBFOX3_ |
| chr05_IL17B_ |
| chr12_GTSF1_ |
| chr01_FMO1_ |
| chr10_NEBL_ |
| chr07_CLEC2L_ |
| chr17_TBX4_ |
| chr10_TACR2_ |
| chr09_TMOD1_ |
| chr20_C20orf166_ |
| chr16_LOC732275_ |
| chr07_TPST1_ |
| chr17_P2RX1_ |
| chr01_HIST2H2BF_ |
| chr02_C2orf40_ |

| Set 3B: ChromosomeName_GeneName |
|---|
| chr10_KCNK18_ |
| chr12_LRP6_ |
| chr19_TARM1_ |
| chr12_NUAK1_ |
| chr15_TJP1_ |
| chr05_HK3_ |
| chr01_NDUFS5_ |
| chr19_CEACAM8_ |
| chr12_BCL2L14_ |
| chr02_AGAP1_ |
| chr06_SLC22A16_ |
| chr04_FAT1_ |
| chr05_PPAP2A_ |
| chr17_CRK_ |
| chr19_LYPD4_ |
| chr10_BMPR1A_ |
| chr14_APOPT1_ |
| chr01_S100A9_ |
| chr19_VSTM1_ |
| chr02_FAM168B_ |
| chr16_MEFV_ |
| chr10_VDAC2_ |
| chr13_FARP1_ |
| chr19_CEACAM4_ |
| chr06_SASH1_ |
| chr03_FLNB_ |
| chr16_ADCY9_ |
| chr03_WWTR1_ |
| chr02_LOC339803_ |
| chr12_SP1_ |
| chr12_LRIG3_ |
| chr13_RNF113B_ |
| chr17_LPO_ |
| chr15_CYFIP1_ |

| Set 3C: ChromosomeName_GeneName |
|---|
| chr10_ZNF503.AS2_ |
| chr05_LRRTM2_ |
| chr02_CCDC140_ |
| chr05_FLJ35946_ |
| chr01_DMRTA2_ |
| chr12_TUBA1A_ |
| chr01_HAPLN2_ |
| chr22_LOC150381_ |
| chr03_ZIC1_ |
| chr01_CAMK2N1_ |
| chr03_EIF4A2_ |
| chr10_VAX1_ |
| chr08_HEY1_ |
| chr11_HSPA8_ |
| chr03_EGOT_ |
| chr17_DDX5_ |
| chr17_TOB1_ |
| chr13_AMER2_ |

| Set 3D: ChromosomeName_GeneName |
|---|
| chr12_KCNA1_ |
| chr02_NPPC_ |
| chr11_ALX4_ |
| chr11_GAL_ |
| chr19_SBK2_ |
| chr18_RBBP8_ |
| chr21_LINC00323_ |
| chr20_TSHZ2_ |
| chr09_LHX6_ |
| chr02_WNT6_ |
| chr01_LRRC71_ |
| chr11_LOC650368_ |
| chr17_PIK3R6_ |
| chr18_GRP_ |
| chr17_RNASEK_ |
| chr05_FOXI1_ |
| chr02_TBR1_ |
| chr01_LOC339505_ |
| chr08_LZTS1.AS1_ |

| Set 3E: ChromosomeName_GeneName |
|---|
| chr14_CBLN3_ |
| chr03_NRADDP_ |
| chr01_SERTAD4.AS1_ |
| chr01_ATPAF1_ |
| chr11_CALCB_ |
| chr16_ZNF764_ |
| chr20_SNRPB2_ |
| chr01_AMIGO1_ |
| chr07_MUC12_ |
| chr16_PDIA2_ |
| chr19_JOSD2_ |
| chr02_IGFBP2_ |
| chr19_HMG20B_ |
| chr22_CHADL_ |
| chr01_DUSP23_ |
| chr22_TUBA3FP_ |
| chr11_KLHL35_ |
| chr06_TOMM6_ |
| chr11_TRPT1_ |
| chr07_NSUN5P1_ |
| chr02_LOC375196_ |
| chr06_LOC729603_ |
| chr19_ANGPTL4_ |
| chr07_NSUN5_ |
| chr13_RBM26.AS1_ |
| chr08_GRINA_ |
| chr01_TSSK3_ |
| chr20_RBBP9_ |
| chr16_PRSS53_ |

| Set 3F: ChromosomeName_GeneName |
|---|
| chr09_DPM2_ |
| chr01_AURKAIP1_ |
| chr01_DCDC2B_ |
| chr01_TAGLN2_ |
| chr02_FAHD2B_ |
| chr11_CDKN1C_ |
| chr22_TNFRSF13C_ |
| chr02_C2orf27B_ |
| chr08_SLURP1_ |
| chr11_TAGLN_ |
| chr17_B4GALNT2_ |
| chr07_RASA4CP_ |
| chr06_SPACA1_ |
| chr19_PAFAH1B3_ |
| chr11_LOC100652768_ |
| chr07_CYCS_ |
| chr17_TLCD1_ |
| chr17_XYLT2_ |
| chr20_PCK1_ |
| chr02_FABP1_ |
| chr17_ACADVL_ |
| chr17_NPTX1_ |
| chr05_TRIM7_ |
| chr16_RPS2_ |
| chr13_NEK3_ |
| chr01_LEFTY1_ |
| chr01_S100A4_ |
| chr03_C3orf45_ |
| chr16_TBC1D10B_ |
| Chr17_GP1BA_ |

| Set 3G: ChromosomeName_GeneName |
|---|
| chr03_CLDN18_ |
| chr02_GKN1_ |
| chr01_CAPN8_ |
| chr21_TFF1_ |
| chr01_FAM177B_ |
| chr02_GKN2_ |
| chr04_ANXA10_ |
| chr02_SULT1C2_ |
| chr08_FER1L6_ |
| chr03_NAALADL2.AS3_ |

| Set 3H: ChromosomeName_GeneName |
|---|
| chr02_TTN.AS1_ |
| chr05_PCDHGA5_ |
| chr05_PCDHGB3_ |
| chr05_PCDHGA6_ |
| chr05_PCDHGA7_ |
| chr05_MIR548AO_ |
| chr05_PCDHGB4_ |
| chr03_SCN5A_ |
| chr19_TNNT1_ |
| chr02_ASB18_ |
| chr05_PCDHGA8_ |
| chr19_ZNF256_ |
| chr03_FGF12_ |
| chr03_FBXO40_ |
| chr05_PCDHGB5_ |

| Set 3I: ChromosomeName_GeneName |
|---|
| chr12_BHLHE41_ |
| chr11_COX8A_ |
| chr02_GBX2_ |
| chr11_FAM181B_ |
| chr10_LINC00200_ |
| chr11_ZNHIT2_ |
| chr01_FAM43B_ |
| chr15_APBA2_ |
| chr21_KCNJ15_ |
| chr10_C10orf114_ |
| chr05_NPR3_ |
| chr07_DPP6_ |
| chr08_ADRB3_ |
| chr18_CDH20_ |
| chr07_ZNF479_ |
| chr09_SSNA1_ |
| chr12_GAPDH_ |
| chr06_QKI_ |
| chr11_NTM_ |
| chr10_ADARB2_ |
| chr04_HMX1_ |
| chr03_LINC00606_ |
| chr11_KIRREL3.AS2_ |
| chr05_C5orf64_ |
| chr08_NKX2.6_ |
| chr11_ASCL2_ |
| chr19_ETV2_ |
| chr18_SALL3_ |
| chr03_ZDHHC23_ |

| Set 3J: ChromosomeName_GeneName |
|---|
| chr10_PAX2_ |
| chr02_GALNT14_ |
| chr12_CCDC64_ |
| chr02_LOC654433_ |
| chr15_PAQR5_ |
| chr01_DNAJC11_ |
| chr12_LOC100130238_ |
| chr02_EMX1_ |
| chr13_C13orf35_ |
| chr16_CDH16_ |
| chr19_FUT3_ |
| chr22_BCRP3_ |
| chr02_PAX8_ |
| chr01_SEMA4A_ |
| chr15_IL16_ |
| chr10_OGDHL_ |
| chr17_LOC284100_ |

| Set 3K: ChromosomeName_GeneName |
|---|
| chr02_APOB_ |
| chr10_CYP2E1_ |
| chr03_ITIH1_ |
| chr05_F12_ |
| chr10_ITIH2_ |
| chr02_ABCG8_ |
| chr11_F2_ |
| chr03_ITIH4_ |
| chr03_NR1I2_ |
| chr17_ASGR2_ |
| chr10_GPAM_ |
| chr15_AQP9_ |
| chr06_PLG_ |
| chr17_SLC13A5_ |
| chr12_AMDHD1_ |
| chr20_LBP_ |

| Set 3L: ChromosomeName_GeneName |
|---|
| chr03_CCR5_ |
| chr06_GPR116_ |
| chr01_TDRD10_ |
| chr01_SHE_ |
| chr10_MYOZ1_ |
| chr15_FAM108C1_ |
| chr19_ICAM5_ |
| chr06_MLLT4.AS1_ |
| chr05_GDNF_ |
| chr04_KDR_ |
| chr12_ALDH2_ |
| chr19_KANK3_ |
| chr12_RILPL2_ |
| chr01_TACSTD2_ |
| chr20_GGTLC1_ |
| chr19_ICAM1_ |

| Set 3M: ChromosomeName_GeneName |
|---|
| chr19_SPIB_ |
| chr12_HVCN1_ |
| chr01_PIK3CD_ |
| chr08_BLK_ |
| chr11_GSTP1_ |
| chr19_FCER2_ |
| chr17_SCIMP_ |
| chr15_LOC388152_ |
| chr19_BST2_ |
| chr07_CARD11_ |
| chr19_CD37_ |
| chr19_NOSIP_ |
| chr07_ATP6V0E2.AS1_ |
| chr09_TRAF1_ |
| chr01_IL10_ |
| chr01_ARHGAP30_ |
| chr16_IL21R.AS1_ |
| chr02_DAPL1_ |
| chr17_ICAM2_ |
| chr05_ITK_ |
| chr08_TNFRSF10A_ |
| chr01_RHD_ |
| chr01_SMAP2_ |
| chr06_TAP1_ |
| chr16_CD19_ |
| chr20_MYBL2_ |

| Set 3N: ChromosomeName_GeneName |
|---|
| chr01_KLHDC8A_ |
| chr02_TCF23_ |
| chr11_WT1_ |
| chr11_AQP11_ |
| chr01_LHX9_ |
| chr07_TSGA13_ |
| chr12_BTBD11_ |
| chr16_CDH3_ |
| chr02_GREB1_ |
| chr17_ATP1B2_ |
| chr01_LEMD1.AS1_ |
| chr05_LOC643201_ |
| chr19_NXNL1_ |

| Set 3O: ChromosomeName_GeneName |
|---|
| chr08_EIF4EBP1_ |
| chr10_SFRP5_ |
| chr01_TMEM51.AS1_ |
| chr19_NPHS1_ |
| chr16_UMOD_ |
| chr01_NR5A2_ |
| chr01_KIAA1324_ |
| chr01_ERO1LB_ |
| chr13_DZIP1_ |
| chr15_HOMER2_ |
| chr04_TMED11P_ |
| chr13_CLDN10_ |
| chr06_LINC00222_ |
| chr20_RBPJL_ |
| chr06_SLC16A10_ |
| chr08_TDH_ |

| Set 3P: ChromosomeName_GeneName |
|---|
| chr19_DPRX_ |
| chr08_CYP7B1_ |
| chr01_HSD3B1_ |
| chr02_ZFP36L2_ |
| chr07_IGF2BP3_ |
| chr18_MBP_ |
| chr13_METTL21C_ |
| chr01_AIM1L_ |
| chr13_WASF3_ |
| chr02_RGPD1_ |
| chr15_CYP19A1_ |
| chr02_RGPD2_ |
| chr01_ADCY10_ |
| chr15_SLCO3A1_ |
| chr07_SLC13A4_ |
| chr16_C16orf45_ |
| chr06_LIN28B_ |
| chr17_RNF222_ |
| chr04_TENM3_ |
| chr15_SH2D7_ |
| chr19_LGALS14_ |
| chr19_CLEC4GP1_ |
| chr16_SPIRE2_ |
| chr08_C8orf42_ |
| chr05_LOC728613_ |

| Set 3Q: ChromosomeName_GeneName |
|---|
| chr22_NEFH_ |
| chr19_KLKP1_ |
| chr06_SPDEF_ |
| chr03_ACPP_ |
| chr18_SLC14A1_ |
| chr19_ZNF350_ |
| chr07_HOXA13_ |
| chr15_SLC30A4_ |
| chr17_KRT14_ |
| chr15_USP50_ |
| chr06_C6orf52_ |
| chr18_OACYLP_ |
| chr19_KLK2_ |
| chr20_EYA2_ |
| chr10_LOC283038_ |
| chr15_LMANIL_ |
| chr02_HOXD10_ |
| chr02_PPP1R7_ |

| Set 3R: ChromosomeName_GeneName |
|---|
| chr14_C14orf177_ |
| chr19_SBSN_ |
| chr06_C6orf132_ |
| chr08_LOC340357_ |
| chr18_CD226_ |
| chr05_AHRR_ |
| chr07_HOXA11.AS_ |
| chr14_BCL11B_ |
| chr06_RAB44_ |
| chr10_FAM25A_ |
| chr05_IRX1_ |
| chr02_SLC35F6_ |
| chr18_RAX_ |
| chr07_MIR548T_ |
| chr12_KRT1_ |
| chr16_HS3ST6_ |
| chr02_PTPN4_ |
| chr07_GPNMB_ |
| Chr17_FAM57A_ |

and

| Set 3S: ChromosomeName_GeneName |
|---|
| chr05_FAM153C_ |
| chr20_DEFB123_ |
| chr16_LITAF_ |
| chr18_ZADH2_ |
| chr09_DMRT1_ |
| chr01_EPS8L3_ |
| chr01_CCDC27_ |
| chr04_SMAD1_ |
| chr11_C11orf91_ |
| chr07_C1GALT1_ |
| chr03_NFKBIZ_ |
| chr20_RIMS4_ |
| chr07_PRSS1_ |
| chr09_OBP2B_ |
| chr12_KRT6A_ |
| chr12_CDK17_ |
| chr21_TEKT4P2_ |
| chr05_ANKRD33B_ |
| chr14_RNASE1_ |
| chr12_PTMS_ |
| chr03_LRRC2_ |
| chr02_SLC30A3_ |
| chr14_IFI27L1_ |
| chr07_C7orf33_. |

16. A method for probabilistically assigning a tissue of origin to cell-free DNA (cfDNA) in a fluid sample obtained from a human subject, comprising:

(a) analyzing the cfDNA in the fluid sample by assessing hydroxymethylation levels within the cfDNA at each of a plurality of hydroxymethylation biomarker loci to generate a sample hydroxymethylation profile, wherein each biomarker locus is contained within a differentially hydroxymethylated genomic region associated with a tissue-specific gene that is both differentially represented and differentially expressed with respect to tissue of origin, and further wherein the biomarker loci analyzed comprise three or more genes selected from the group consisting of AARD, ADARB1, AKR1B10, CRYM-AS1, EPHA3, GTSF1, KCNMB1, MAP1B, NT5DC3, P2RX1, PCP4, PGM5, PLCD4, PTGFR, RBFOX3, SCARA3, SLIT3, SNX29P1, ST8SIA1, TBX4, TXNRD1, VCL, and WFDC3;

three or more genes selected from the group consisting of ABCA13, AZU1, CA1, CEACAM8, CLEC6A, DAZL, DRGX, DYTN, ELANE, FCAR, GFI1, GYPA, HK3, IL18RAP, LINC00333, LINC00550, LINC00558, LIPN, LOC100129620, LOC442028, LPO, MEFV, MMP8, MMP9, MPO, MS4A3, MYB, MYO1F, NCOR1P1, NME8, OR8U8, OSCAR, PARPBP, PAX3, PDCL2, PRDM13, PROK2, RGS18, RGS21, RRM2, RXFP2, SERPINB10, SLC22A16, SPATA16, SPI1, SPTA1, TARM1, TMPRSS15, TRIM58, VSTM1, and XKR;

three or more genes selected from the group consisting of ASPHD1, BRSK1, CCDC177, CNTN2, HAPLN2, KCNJ10, KIF1A, LGI3, NCAN, NR2E1, RHBDL3, TMEM151A, TMEM235, TMEM59L, and ZNF488;

three or more genes selected from the group consisting of ADPRHL1, ASB18, ATP1A3, CDH13, CORO6, FSD2, GALNT16, GJA3, MYOM2, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB5, PCDHGB6, PCDHGB7, PXDNL, RPL3L, SGCG, and TNNT1;

three or more genes selected from the group consisting of BBOX1, BCRP3, CA12, COL4A3, CXCL14, CYS1, EVC, FIGNL2, GALNT14, GLIS2, HAVCR1, LOC100130238, PAQR5, PAX2, PAX8, PLA2G15, SLC22A2, SLC9A3, SULT1C2, and TSPAN33;

three or more genes selected from the group consisting of ABCC2, ABCG5, ABCG8, AHSG, AKR1C4, AMDHD1, APOH, ASGR1, ASGR2, C3P1, C8A, C8B, C9, CA5A, CFHR4, CPN2, CREB3L3, CYP2B6, CYP2C9, CYP2E1, CYP3A4, DHODH, F12, F2, F7, GC, HAL, HPD, HPX, INHBC, ITIH1, ITIH2, ITIH3, KNG1, LBP, PGLYRP2, PLG, PROC, PRODH2, SERPINA6, SERPINC1, SLC13A5, SLC22A1, SLC25A47, SLC27A5, SULT2A1, TFR2, TMPRSS6, and UROC1;

three or more genes selected from the group consisting of ANXA3, BMP5, CYP4Z2P, DRAM1, FMO2, GNA15, IDO1, KCNS3, LIMCH1, MBIP, PAPSS2, PCDH17, RSPH4A, RTKN2, and TRPC6;

three or more genes selected from the group consisting of ACAP1, AKNA, ARHGAP9, BCL11B, BIRC3, CARD11, CD180, CD37, CD3E, CD3G, CD40, CETP, CIITA, CLEC2D, CNR2, CXCR5, DOCK10, ETS1, GPR132, GPR18, ICAM2, ICOS, ITGB7, ITK, KIAA1551, KLHL6, LCK, LINC00426, LY86, MDS2, MEOX2, MX2, NAPSB, PATL2, PCED1B-AS1, PIK3CD, PLVAP, POU2F2, SCIMP, SCML4, SLFN12L, SMAP2, SP110, SPIB, TLR10, TMC8, TMEM156, TNFAIP8, TNFRSF9, TNFSF11, TRAF1, TRIM22, UCP2, and ZC3H12D;

three or more genes selected from the group consisting of ABCA10, ACSS3, ADAMTS5, AQP11, C7, CDH3, CDON, CLDN11, COL14A1, COLEC11, ESR2, FAM198B, FZD3, GALNT10, GLI2, GSTM5, HS3ST1, LEMD1-AS1, LHX9, LRRC17, MCHR1, MRC2, NTF3, OMD, PDGFRA, PGR, PKNOX2, PTCH2, RWDD4, SCD5, SERPINE2, SIMC1, SLC25A17, SNCAIP, SULF2, TENM4, TSPAN5, TTC8, and UBXN8;

three or more genes selected from the group consisting of ALDH1L2, ANKEF1, ASNS, B3GALNT2, BCAT1, CASP9, CCDC110, CELA2B, CELA3B, CFTR, CHMP4C, CLDN1, CNIH3, COCH, CUZD1, DEFB1, EGF, EIF4EBP1, ERP27, FAM24B-CUZD1, FBXW12, GUCA1C, KCTD16, KIAA1324, LINC00339, LNX2, MKNK1, NAA16, NPHS1, PAIP2B, PM20D1, PRSS3, SCGN, SEL1L, SERPINI2, SH3YL1, SLC33A1, SLC4A4, TC2N, TDH, TMEM51-AS1, TRHDE, and UMOD;

three or more genes selected from the group consisting of ADAM12, ATG9B, ATP6V1C2, BCAR4, BMP1, BPGM, CSF3R, CYP11A1, CYP19A1, DACT2, DEPDC1B, DLX5, EBI3, GCM1, GPR78, GSTA3, IGF2BP3, IGSF5, ISM2, KISS1, KRT23, LIN28B, MMP11, PGF, PSG11, PSG2, PSG3, PSG6, PSG7, PSG8, SPTLC3, TPRXL, ZFAT, and ZNF554;

three or more genes selected from the group consisting of ABCC4, ACPP, ALOX15B, ANO7, AP1B1P1, ARG2, BEND4, C6orf132, C6orf52, CANT1, CASZ1, CBFA2T2, CHRM1, CHRNA2, COL26A1, EVX1, EYA2, FAM135A, HMGN2P46, KLK2, KLKP1, MME, MPPED2, MUC12, NANS, NCAPD3, NEFH, NIPAL3, OACYLP, OR51E2, PAK1IP1, PDE9A, PI15, PMEPA1, POTEF, RDH11, SCNN1G, SIM2, SLC14A1, SLC22A3, SLC2A12, SLC30A4, SLC35F2, SLC37A1, SLC39A6, SPDEF, STEAP2, THSD4, TMEM79, TPM3P9, TXNDC16, URB1, VIPR1, ZNF350, ZNF532, ZNF613, ZNF649, ZNF761, and ZNF827;

three or more genes selected from the group consisting of GADL1, GIPC3, PTGES3L, and WSCD2;

three or more genes selected from the group consisting of CCDC27, DMRT1, DNAJC5G, FBXO24, IGLL1, MOV10L1, SEPT14, THEG, and TTC16;

at least one gene selected from FGL2 and SCNN1B; and at least one gene selected from ASTN1 and DGK1;

(b) comparing each assessed hydroxymethylation level in the sample hydroxymethylation profile with a corresponding reference hydroxymethylation level at each biomarker locus analyzed, the reference hydroxymethylation levels being contained within a plurality of different tissue-specific reference hydroxymethylation profiles in a reference data set, thereby generating a hydroxymethylation difference data set comprising differences identified between the generated sample hydroxymethylation profile and the reference hydroxymethylation profiles at each biomarker locus;

(c) using a computer system, carrying out a correlation analysis using one or more algorithms that determine a statistical correlation between the assessed hydroxymethylation levels and the reference hydroxymethylation levels at each biomarker locus; and (d) using the statistical correlation, providing a probabilistic assignment of at least one tissue of origin to the cfDNA.

* * * * *